United States Patent
Gascoyne et al.

(10) Patent No.: US 7,175,086 B2
(45) Date of Patent: Feb. 13, 2007

(54) AUTHENTICATION SYSTEM, DATA DEVICE, AND METHODS FOR USING THE SAME

(75) Inventors: David Gascoyne, Schnectady, NY (US); Brian Lawrence, Clifton Park, NY (US); Sriramakrishna Maruvada, Evansville, IN (US); Radislav Potyrailo, Niskayuna, NY (US); Philippe Schottland, Evansville, IN (US); Micah Sakiestewa Sze, Albany, NY (US); Marc Brian Wisnudel, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 120 days.

(21) Appl. No.: 10/709,208

(22) Filed: Apr. 21, 2004

(65) Prior Publication Data

US 2005/0236481 A1    Oct. 27, 2005

(51) Int. Cl.
    G06K 7/10    (2006.01)
    G06K 7/14    (2006.01)
    G01J 1/58    (2006.01)
    G01N 21/64   (2006.01)
    G01T 1/00    (2006.01)

(52) U.S. Cl. .............. 235/454; 369/275.2; 250/486.1

(58) Field of Classification Search ........ 235/435, 235/454; 369/275.2, 121, 128, 116; 396/18, 396/211, 57, 429, 284; 360/69, 133, 70; 250/458.1, 459.1, 462.1, 483.1, 486.1, 487.1, 250/214 S, 484.2

See application file for complete search history.

(56) References Cited

U.S. PATENT DOCUMENTS

| | | | |
|---|---|---|---|
| 3,635,895 A | 1/1972 | Kramer et al. | 260/47 XA |
| 3,928,226 A | 12/1975 | McDonough et al. | |
| 4,001,184 A | 1/1977 | Scott | 260/47 XA |
| 4,127,773 A | 11/1978 | West | |
| 4,217,438 A | 8/1980 | Brunelle et al. | 528/202 |
| 4,238,524 A | 12/1980 | LaLiberte et al. | 427/7 |
| 4,600,632 A | 7/1986 | Paul et al. | 428/220 |
| 4,699,510 A | 10/1987 | Alguard | 356/73 |

(Continued)

FOREIGN PATENT DOCUMENTS

EP    0121261 A2    10/1984

(Continued)

OTHER PUBLICATIONS http://www.taosinc.com/product_detaiol.asp?cateid=11&proid+12; "Color Sensors"; TAOSin / Texas Advanced Optoelectronic Solutions; Feb. 23, 2004 (1 page).

(Continued)

*Primary Examiner*—Thien M. Le
*Assistant Examiner*—Thien T. Mai

(57) ABSTRACT

An authentication system may comprise: a first light source, a second light source, and at least three optically filtered light sensing devices. The first light source can have a first light source spectral distribution and can be capable of providing sufficient excitation to produce a photoluminescent emission from a medium comprising a luminescent tag and a color. The second light source can have a visible multi-wavelength spectral distribution and can be capable of providing sufficient visible multi-wavelength illumination of the medium to generate a second analog response. Each light sensing device can have a different device spectral sensitivity range.

37 Claims, 12 Drawing Sheets

U.S. PATENT DOCUMENTS

| | | | |
|---|---|---|---|
| 4,774,315 A | 9/1988 | Miller | |
| 5,005,873 A | 4/1991 | West | 283/92 |
| 5,028,690 A | 7/1991 | Gallucci | |
| 5,043,203 A | 8/1991 | Fyvie et al. | |
| 5,137,364 A | 8/1992 | McCarthy | 356/402 |
| 5,142,018 A | 8/1992 | Sakashita et al. | 528/199 |
| 5,151,491 A | 9/1992 | Sakashita et al. | 528/199 |
| 5,201,921 A | 4/1993 | Luttermann et al. | 8/506 |
| 5,314,072 A | 5/1994 | Frankel et al. | 209/44.1 |
| 5,326,692 A | 7/1994 | Brinkley et al. | 435/6 |
| 5,329,127 A | 7/1994 | Becker et al. | 250/459.1 |
| 5,356,668 A | 10/1994 | Paton et al. | |
| 5,380,795 A | 1/1995 | Gosens et al. | 525/67 |
| 5,510,619 A | 4/1996 | Zachmann et al. | 250/339.08 |
| 5,532,998 A * | 7/1996 | Durham | 369/116 |
| 5,548,106 A * | 8/1996 | Liang et al. | 235/454 |
| 5,553,714 A | 9/1996 | Cushman et al. | 209/577 |
| 5,573,909 A | 11/1996 | Singer et al. | 435/6 |
| 5,640,010 A | 6/1997 | Twerenbold | |
| 5,644,017 A | 7/1997 | Drumright et al. | |
| 5,668,202 A | 9/1997 | Hirata et al. | |
| 5,703,229 A | 12/1997 | Krutak et al. | 540/140 |
| 5,706,266 A | 1/1998 | Brownstein et al. | |
| 5,815,484 A | 9/1998 | Smith et al. | |
| 5,838,451 A | 11/1998 | McCarthy | 356/406 |
| 5,892,577 A | 4/1999 | Gordon | |
| 5,918,960 A | 7/1999 | Hopwood et al. | |
| 6,099,930 A | 8/2000 | Cyr et al. | 428/64.1 |
| 6,160,787 A | 12/2000 | Marquardt, Jr. et al. | 369/275.1 |
| 6,181,662 B1 * | 1/2001 | Krieger et al. | 369/70 |
| 6,219,329 B1 | 4/2001 | Tanaka et al. | |
| 6,326,605 B1 * | 12/2001 | Modlin et al. | 250/214 SW |
| 6,327,031 B1 | 12/2001 | Gordon | |
| 6,342,349 B1 | 1/2002 | Virtanen | |
| 6,355,420 B1 | 3/2002 | Chan | |
| 6,380,547 B1 * | 4/2002 | Gonzalez et al. | 250/458.1 |
| 6,469,969 B2 | 10/2002 | Carson et al. | |
| 6,500,547 B1 | 12/2002 | Potyralio et al. | |
| 6,514,617 B1 | 2/2003 | Hubbard et al. | 428/412 |
| 6,543,351 B2 | 4/2003 | Haycock et al. | 702/127 |
| 6,589,626 B2 | 7/2003 | Selinfreund et al. | 428/64.1 |
| 6,603,126 B2 | 8/2003 | Yamada et al. | 250/372 |
| 6,612,494 B1 | 9/2003 | Outwater | |
| 6,638,593 B2 | 10/2003 | Selinfreund et al. | 428/64.1 |
| 6,707,539 B2 | 3/2004 | Selinfreund et al. | 356/71 |
| 2002/0025490 A1 * | 2/2002 | Shchegolikhin et al. | 430/270.15 |
| 2002/0173040 A1 | 11/2002 | Potyrailo et al. | |
| 2003/0012562 A1 | 1/2003 | Lawandy et al. | 386/126 |
| 2003/0076775 A1 | 4/2003 | Sato et al. | |
| 2003/0136837 A1 * | 7/2003 | Amon et al. | 235/435 |
| 2004/0058058 A1 * | 3/2004 | Shchegolikhin et al. | 427/7 |
| 2004/0083377 A1 | 4/2004 | Wu et al. | |
| 2004/0094626 A1 * | 5/2004 | Sillman et al. | 235/462.15 |
| 2004/0156081 A1 * | 8/2004 | Bril et al. | 358/3.28 |
| 2005/0026154 A1 * | 2/2005 | Bruhn et al. | 435/6 |
| 2005/0109984 A1 | 5/2005 | Potyrailo | |
| 2005/0110993 A1 * | 5/2005 | Dorsel | 356/318 |
| 2005/0111342 A1 | 5/2005 | Wisnudel et al. | |
| 2005/0163026 A1 * | 7/2005 | Oshima et al. | 369/275.2 |

FOREIGN PATENT DOCUMENTS

| | | |
|---|---|---|
| EP | 0181228 B1 | 5/1986 |
| EP | 0 438 225 B1 | 7/1991 |
| EP | 0990890 A1 | 4/2000 |
| EP | 1178429 A2 | 2/2002 |
| EP | 1 189 062 A1 | 3/2002 |
| EP | 1220165 A2 | 7/2002 |
| GB | 1170965 | 11/1969 |
| GB | 2264558 A | 9/1993 |
| GB | 2330408 A | 4/1999 |
| WO | WO 98/12559 | 3/1998 |
| WO | WO 98/31011 | 7/1998 |
| WO | WO 99/35499 | 7/1999 |
| WO | WO 00/14734 | 3/2000 |
| WO | WO 00/14736 | 3/2000 |
| WO | WO 0171646 A1 | 9/2001 |
| WO | WO 00/21086 | 4/2002 |
| WO | WO 03/087888 A2 | 10/2003 |
| WO | WO 03/105075 | 12/2003 |

OTHER PUBLICATIONS

Kevin M. Cantrell, et al.; "The SLIM Spectrometer"; Analytical Chemistry, vol. 75, No. 1, Jan. 1, 2003, pp. 27-35.

Billboard, 114, 43, 46(1); Oct. 26, 2003; ISSN: 0006-2510; Copyright 2002 VNU Business Media; Universal Italy initiatives encorage price cutting: president/CEO calls for other labels to follow his company's lead. (International) 1 page.

Letters to the Editor, Financial Times, USA Ed1 20021119U112.036 ed, p. 12; Nov. 19, 2002; Journal Code: FFT; Industry Fails to provide user-friendly music 1 page.

Online Reporter, p NA; Aug. 23, 2003; Newsletter (United States) Kviar Sees Custom CD Kiosks All over Brazil; Copyright 2003 G2 Intelligence, Inc. (1 page).

South China Morning Post, p11, Jul. 17, 2001; "Creative thinking the magic ingredient for modest enterprises looking to establish their own market niche Spark of originality fires smart ventures"; Copyright 2001 (2 pages).

JP 2000076659; Mar. 14, 2000; English Abstract only; 1 page.

USCD Scientists Develop Novel Way to Screen Molecules Using Conventional CDs and Compact Disk Players, Science and Engineering UCSD Press Release, Aug. 20, 2003.

La Clair, et al., "Molecular Screening on a compact disc," Orig. Biomol. Chem. 2003, 1 (Advance Article)(Abstract).

La Clair, et al., "Molecular Screening on a compact disc," Org. Biomol. 2003, 1, (Advance Article)(Paper).

Duffy, et al. "Microfabricated Centrifugal Microfluidic Systems: Characterization and Multiple Enzymatic Assays," anal. Chem. 71:4669-4678 (1999).

La Clair, et al., "Molecular Screening on a compact disc." Org. Biomol. Chem. 2003, 1:3244-3249.

International Search Report; International Application No. PCT/US2004/035029; Applicant's File Reference 08CL 140323; International Filing Date Oct. 22, 2004; Date of Mailing Apr. 22, 2005.

U.S. Appl. No. 10/889,913, filed Jul. 13, 2004; Sriramakrishna Maruvada et al.; Authenticatable Article and Method of Authenticating (Available in Image File Wrapper (IFW)).

U.S. Appl. No. 10/987,282, filed Nov. 12, 2004; van de Grampel et al.; Authenticatable Media and Method of Authenticating (Available in Image File Wrapper (IFW)).

U.S. Appl. No. 10/723,682, filed Nov. 24, 2003, Marc Wisnudel et al., "Authenticable Optical Dis. System for Authenticating and Optical Disc and Method Thereof", 20 pages.

International Search Report; International Application No. PCT/US2005/013353; International Search Date Jul. 4, 2005; Date of Mailing Sep. 9, 2005.

* cited by examiner

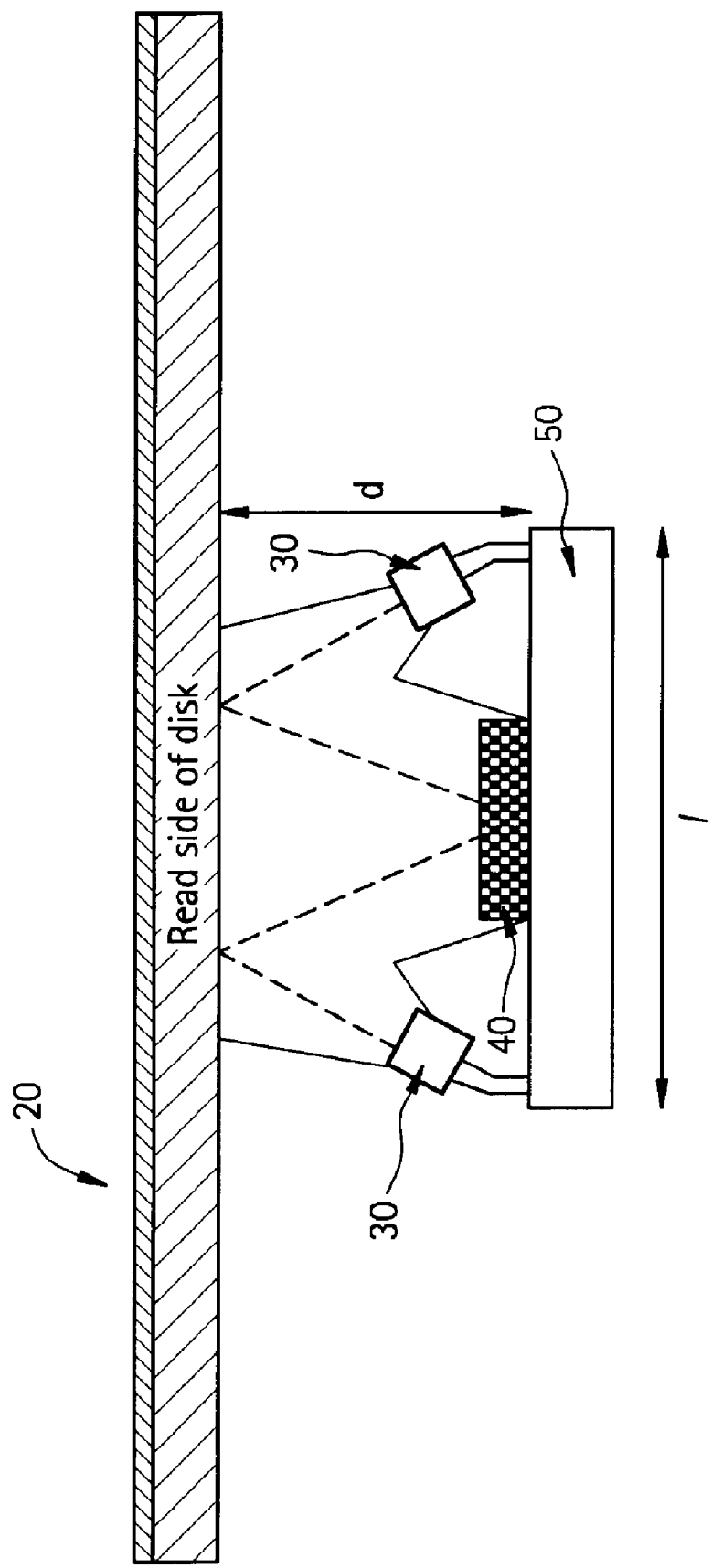

Color Determination

Fluorescence Determination

AUTHENTICATION SYSTEM, DATA DEVICE, AND METHODS FOR USING THE SAME

BACKGROUND OF THE INVENTION

In the field of data storage media, digital content owners, such as music companies, movie studios, video game manufacturers, computer software manufacturers, and the like, desire increased flexibility in the distribution of their digital content onto various forms of data storage media. Digital content kiosks are becoming an increasingly popular means for displaying, and in some cases, distributing digital content. Commercially available digital content kiosks utilize a variety of data storage media. However, because these data storage media are pre-mastered, the choice of digital content available to a user is often limited. The costly manufacturing and replication process associated with the data storage media necessitates the production of hundreds to thousands of the data storage media in order to make the production process cost-effective. Thus, the production and distribution of individual or small lots of pre-mastered data storage media is cost-prohibitive.

One possible solution to this problem is the use of write-once or rewritable formats. Such data storage media would allow for the "on-demand" distribution of digital content, expanding the choice of digital content available to a user and eliminating the need for the production of hundreds to thousands of pre-mastered data storage media. However, these data storage media may provide little protection for a digital content owner's intellectual property. A major problem confronting the various makers and users of non-recordable and recordable data storage media such as compact discs (CD), digital versatile discs (DVD), enhanced video discs (EVD), recordable compact discs (CD-R) and recordable digital versatile discs (DVD-R) is the unauthorized reproduction or copying of information by unauthorized manufacturers, sellers, and/or users. Such unauthorized reproduction or duplication of data storage media is often referred to as piracy. Piracy may occur in a variety of ways, including consumer level piracy at the point of end use as well as wholesale duplication of data, substrate and anti-piracy information at the commercial level. Regardless of the manner, piracy of data storage media deprives legitimate digital content providers and manufacturers of significant revenue and profit.

Attempts to stop piracy at the consumer level have included the placement of electronic anti-piracy signals on information carrying substrates along with the information sought to be protected. The machine readers and players of such data storage media are configured to require the identification of such anti-piracy signals prior to allowing access to the desired information. Theoretically, consumer level duplications are unable to reproduce these electronic anti-piracy signals on unauthorized copies and hence result in duplicates and copies that are unusable.

However, numerous technologies to thwart such consumer level anti-piracy technologies have been and continue to be developed. Moreover, commercial level duplications have evolved to the point that unauthorized duplicates may now contain the original electronic anti-piracy circuit, code, etc. For example, commercial level duplication methods include pit copying, radio frequency (RF) copying, "bit to bit" copying and other mirror image copying techniques which result in the placement of the anti-piracy signal on the information carrying substrate of the duplicate along with the information sought to be protected. Other technologies commonly used by hackers include the modification of the computer code in order to remove anti-piracy (also referred to as copy-protection or copy-proofing) features and enable unlimited access to the data.

It would be desirable to have a data storage media that can be easily identified as to being authentic or pirated. One anti-piracy technology aimed at combating these more sophisticated consumer and commercial level reproduction and copying practices involves the placement of 'tags' or authentication markers in substrates used in the construction of data storage media. Such tags or authentication markers can be detected at one or more points along the data storage media manufacturing or distribution chain or by the end use reader or player used to access the data on a particular data storage media.

The automated identification of plastic compositions used in data storage media is very desirable for a variety of applications, such as recycling, tracking the manufacturing source, antipiracy protection, and others. Furthermore, it may be desirable for automated authentication of the data storage media.

Despite the foregoing, there still remains a desire for an authentication detector that may be effectively incorporated into a digital content kiosk machine and a method for using the same.

SUMMARY

This disclosure relates to an authentication system, a data device, and a method of using the data device. In one embodiment, the authentication system comprises: a first light source, a second light source, and at least three optically filtered light sensing devices for detecting analog emission intensity in a spectral sensitivity range, wherein each light sensing device is in operable communication with the first light source and/or the second light source. The first light source can have a first light source spectral distribution and can be capable of providing sufficient excitation to produce a photoluminescent emission from a medium comprising a fluorophore and a color. The second light source can have a visible multi-wavelength spectral distribution and can be capable of providing sufficient visible multi-wavelength illumination of the medium to generate a second analog response, wherein the second analog response is different from the photoluminescent emission. Each light sensing device can have a different device spectral sensitivity range which includes at least a portion of the visible multi-wavelength spectral distribution, with the device spectral sensitivity range of at least one of the light sensing devices including at least a portion of a desired photoluminescent emission wavelength range.

In one embodiment, the data device comprises: an authentication analog measurement device capable of generating a detected analog signature of a data storage medium; a comparator capable of determining if the detected analog signature is from an authentic medium, wherein the comparator is in operable communication with the measurement device; and an information device capable of at least one of reading from and writing to the authentic medium, wherein the information device is in operable communication with the comparator.

In one embodiment, the method of using the data device comprises: illuminating a tested medium with a first light source to produce a tested photoluminescent emission; illuminating the tested medium with a second light source in the visible wavelength range to produce a second analog response, wherein the second analog response is different from the tested photoluminescent emission; determining a first intensity of the tested photoluminescent emission, wherein the first intensity is determined in a first wavelength range that includes the desired photoluminescent peak intensity; determining a second intensity of the tested photoluminescent emission, wherein the second intensity is determined in a second wavelength range that is different than the first wavelength range; determining a third intensity of the tested photoluminescent emission, wherein the third intensity is determined in a third wavelength range that is different than the first and second wavelength range; determining if the first intensity, the second intensity, and the third intensity of the tested photoluminescent emission correspond to the optical photoluminescence identifier; and determining if the second analog response corresponds to the optical color identifier. If the first intensity, the second intensity, and the third intensity correspond to the optical photoluminescence identifier and if the second analog response corresponds to the optical color identifier, the tested medium is authenticated as the authentic medium.

In another embodiment, the method of using a data device, comprises: generating a detected analog signature from a data storage medium; comparing the detected analog signature to a desired signature from an authentic medium; determining if the detected analog signature is from an authentic medium; and controlling an information device based upon whether the detected analog signature is from the authentic medium, such that if the detected analog signature is from the authentic medium, the information device at least one of reads from and writes to the authentic medium, and if the detected analog signature is from an non-authentic medium, the information device is inhibited from reading from and writing to the non-authentic medium.

The above described and other features are exemplified by the following figures and detailed description.

BRIEF DESCRIPTION OF THE DRAWINGS

Refer now to the figures, which are exemplary embodiments, and wherein the like elements are numbered alike.

FIG. 4 is a schematic side view of an exemplary embodiment of an authentication device operating in the reflectance mode with the light sources disposed at angles to the circuit board and to the media.

DETAILED DESCRIPTION

Figure 1:
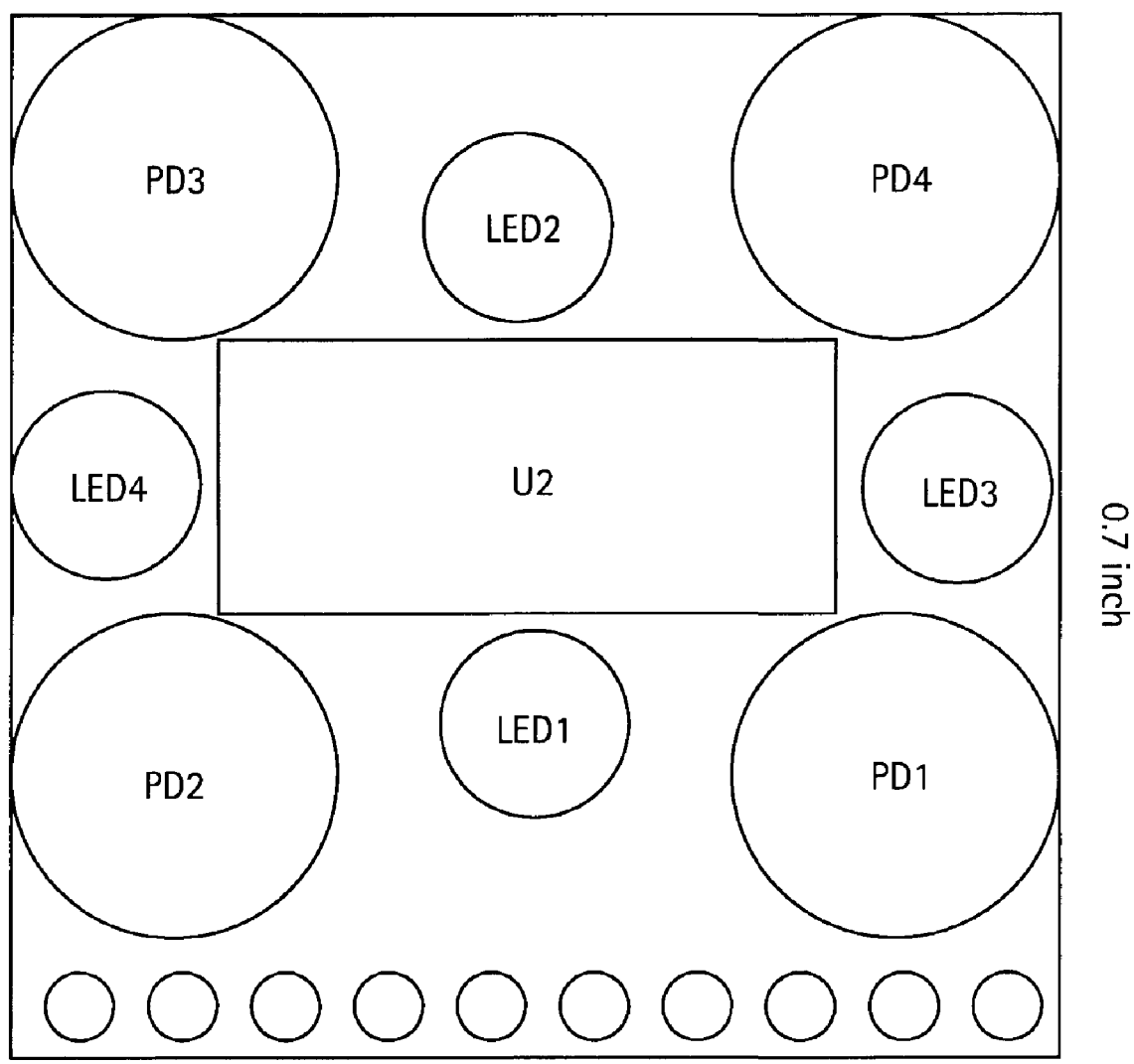
FIG. 1 is a top view schematic illustration of one embodiment of an authentication device.

It is noted that the terms "first," "second," and the like, herein do not denote any amount, order, or importance, but rather are used to distinguish one element from another, and the terms "a" and "an" herein do not denote a limitation of quantity, but rather denote the presence of at least one of the referenced item. Additionally, all ranges disclosed herein are inclusive and combinable (e.g., the ranges of "up to 25 wt %, with 5 wt % to 20 wt % desired," are inclusive of the endpoints and all intermediate values of the ranges of "5 wt % to 25 wt %," etc.). "Color" in a medium is intended to mean that at least a portion of the visible energy directed at the medium is affected by the medium. The visible energy can be affected for example, by absorption, scattering, diffusion and/or reflection of certain wavelengths, thus creating the "color". Note that even a "colorless/clear" medium or a medium with a parts per million range loading of blue dye will absorb light and therefore comprise a "color". Similarly, a metal reflective layer or a CD-R dye interacts with a visible light source, so any medium including any of these are considered to comprise a "color".

An authentication system can comprise: a first light source, a second light source, and at least three optically filtered light sensing devices in operable communication with the first light source and the second light source. Optionally, these light sensing devices can be oriented to operate in a reflectance mode where the first light source and the second light source are disposed adjacent to the light sensing devices. When an authentic medium is tested in the system, the first light source is capable of providing sufficient excitation to produce a photoluminescent emission from the medium (e.g., from the read side of a data storage medium substrate, where the substrate, a label, and/or a layer on the substrate, individually, comprise a fluorophore and/or a color). The second light source is capable of providing sufficient visible multi-wavelength illumination of the substrate to generate a second analog response that is different from the photoluminescent emission (e.g., such that the affect on the visible multi-wavelength illumination (hereinafter referred to as "the color") can be detected).

Desirably, each light sensing device has a different device spectral sensitivity range that at least includes a portion of the visible multi-wavelength spectral distribution. Additionally, the device spectral sensitivity range of at least one of the light sensing devices includes at least a portion of a desired photoluminescent emission wavelength range (i.e., the photoluminescent emission wavelength range emitted by an authentic medium). Desirably, at least one of the light sensing devices includes a desired photoluminescence near peak emission wavelength (i.e., ±20 nm from the desired peak photoluminescent emission wavelength), with at least one of the light sensing devices including the desired photoluminescence peak emission wavelength more desirable. It is noted that the spectral sensitivity ranges of the light sensing devices can overlap, but are not equal.

In one embodiment, authentication of data storage media can be accomplished using an authentication system having at least three optically filtered light sensing devices and two energy sources. One or more of the energy sources can be energy (e.g., electromagnetic radiation (i.e., light) sources such as lamps, lasers, light emitting diodes (LEDs), and the like) provided by a data storage media device (e.g., a CD and DVD player, and the like) or can be part of the authentication system. Therefore, the authentication system can be employed in various detection applications and devices, including kiosk machines (e.g., machines capable of disposing audio and/or visual data selected from a content library onto a disc), optical drives (e.g., CD/DVD devices, and the like), credit card/debit card readers, passport readers, casino chip authentication devices, part authentication/sorting machines, and the like.

In another embodiment, the authentication system can be an authentication device that is part of a data device (e.g., a device capable of reading from and/or writing to a data storage medium (wherein writing to includes all forms of disposing data onto/in the medium)). In this application, the authentication device is capable of generating one or more detected analog signature(s) from a read side of a data storage medium, with two or more signatures preferred. The measurement device can measure a response to a property of energy (e.g., light, radio frequency, radioactive, magnetic, and/or electrical, and the like, with light generally preferred). A detected signature generated from the property of energy is used by a comparator capable of determining if the detected signature is from an authentic medium. This comparator is in operable communication with the measurement device and with an information device. The information device is capable of reading from and/or writing to the authentic medium, in one or more sessions and is in operable communication with the comparator. The comparator can accept (authentic) or reject (non-authentic) the medium so that the information device will read from/write to the medium or refuse to read from/write to the medium. Optionally, the data device can have a medium holder (e.g., such that data storage media can be stored in the device for future use), and/or a handling system (e.g., for receiving the data storage medium from an external source (such as a recordable or rewritable optical disc (e.g., a medium that does not contain data (music, video (e.g., movie, movie preview, game, etc.), digital photograph, computer software, data files, music . . . ), but may contain digital identification information) inserted by a customer into a kiosk machine). Optionally, the data device can employ the authentication system as the authentication device.

Any article that can be received in the authentication system can be authenticated. The authentic article should have a tag that, when contacted by energy, produces a readable property of energy that can be compared to a reference signature. For example, exemplary data storage media include media that are capable of producing a detectable signature (e.g., detectable photoluminescent emission (e.g., a medium comprising a tag or optical identifier), and/or other detectable property of energy). Data storage media include, for example, optical and magneto-optical media formats, such as compact discs (CD) (e.g., recordable compact disc (CD-R), rewritable compact disc (CD-RW), and the like), magneto-optical discs, digital versatile discs (e.g., DVD-5, DVD-9, DVD-10, DVD-18, DVD-R, DVD-RW, DVD+RW, DVD-RAM, HD-DVD, and the like), Blu-Ray discs, enhanced video discs (EVD), and recordable and re-writable Blu-Ray discs, and the like. The detectable photoluminescence can be produced from any portion of the media, e.g., a substrate, coating, bonding layer, and/or the like. Generally, the data storage media comprises a substrate, with one or more data storage portions(s) (e.g., magnetic, magneto-optic, optic, and the like; wherein the portion may be a layer of material and/or surface features (pits, grooves, lands, and the like)), protective layer(s), dielectric layer(s), insulating layer(s), combinations comprising at least one of the foregoing, and others.

Examples of substrates include, amorphous, crystalline, and/or semi-crystalline thermoplastic materials, such as: polyvinyl chloride, polyolefins (including linear and cyclic polyolefins and including polyethylene, chlorinated polyethylene, polypropylene, and the like), polyesters (including polyethylene terephthalate, polybutylene terephthalate, polycyclohexylmethylene terephthalate, and the like), polyamides, polysulfones (including hydrogenated polysulfones, and the like), polyimides, polyether imides, polyether sulfones, polyphenylene sulfides, polyether ketones, polyether ether ketones, ABS resins, polystyrenes (including hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including polymethylmethacrylate, methyl methacrylatepolyimide copolymers, and the like), polyacrylonitrile, polyacetals, polycarbonates, polyphenylene ethers (including those derived from 2,6-dimethylphenol and copolymers with 2,3,6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, polytetrafluorethylene, as well as thermosetting resins such as epoxy, phenolic, alkyds, polyester, polyimide, polyurethane, mineral filled silicone, bis-maleimides, cyanate esters, vinyl, and benzocyclobutene resins, in addition to combinations, blends, copolymers, mixtures, reaction products, and composites comprising at least one of the foregoing.

As used herein, the terms "polycarbonate", "polycarbonate composition", and "composition comprising aromatic carbonate chain units" includes compositions having structural units of the formula (1):

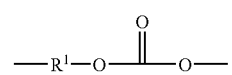

(I)

In Which Greater than or Equal to about 60 Percent of the Total Number of $R^1$ Groups are Aromatic Organic Radicals and the Balance thereof are Aliphatic, Alicyclic, or Aromatic Radicals.

Polycarbonates can be produced by various methods including interfacial, melt, activated carbonate melt, and solid-state processes. For example, polycarbonate can be produced by the interfacial reaction of dihydroxy compounds. Preferably, $R^1$ is an aromatic organic radical and, more preferably, a radical of the formula (II):

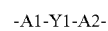 (II)

wherein each of $A^1$ and $A^2$ is a monocyclic divalent aryl radical and $Y^1$ is a bridging radical having one or two atoms which separate $A^1$ from $A^2$. In one embodiment, one atom separates $A^1$ from $A^2$. Illustrative, non-limiting examples of radicals of this type are —O—, —S—, —S(O)—, —S(O$_2$)—, —C(O)—, methylene, cyclohexyl-methylene, 2-[2,2,1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene or isopropylidene.

Polycarbonates can be produced by the interfacial reaction of dihydroxy compounds in which only one atom separates $A^1$ and $A^2$. As used herein, the term "dihydroxy compound" includes, for example, bisphenol compounds having general formula (III) as follows:

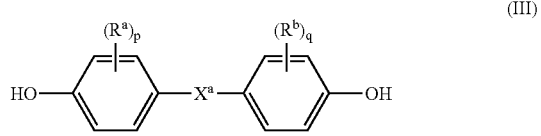

(III)

wherein $R^a$ and $R^b$ each represent a halogen atom or a monovalent hydrocarbon group and may be the same or different; p and q are each independently integers from 0 to 4; and $X^a$ represents one of the groups of formula (IV):

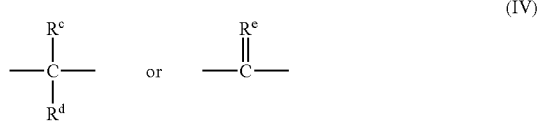

(IV)

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include dihydric phenols and the dihydroxy-substituted aromatic hydrocarbons disclosed by name or formula (generic or specific) in U.S. Pat. No. 4,217,438 the contents of which are hereby incorporated by reference in their entirety. A nonexclusive list of specific examples of the types of dihydroxy compounds that may be represented by formula (III) includes the following:
1,1-bis(4-hydroxyphenyl)methane;
1,1-bis(4-hydroxyphenyl)ethane;
2,2-bis(4-hydroxyphenyl)propane (hereinafter "bisphenol A" or "BPA"); 2,2-bis(4-hydroxyphenyl)butane;
2,2-bis(4-hydroxyphenyl)octane;
1,1-bis(4-hydroxyphenyl)propane;
1,1-bis(4-hydroxyphenyl)$_n$-butane;
bis(4-hydroxyphenyl)phenylmethane;
2,2-bis(4-hydroxy-1-methylphenyl)propane;
1,1-bis(4-hydroxy-t-butylphenyl)propane;
2,2-bis(4-hydroxy-3-bromophenyl)propane;
1,1-bis(4-hydroxyphenyl)cyclopentane; such as
1,1-bis(4-hydroxyphenyl)cyclohexane; and the like, as well as combinations comprising at least one of the foregoing.

It is also possible to employ polycarbonates resulting from the polymerization of two or more different dihydric phenols or a copolymer of a dihydric phenol with a glycol or with a hydroxy- or acid-terminated polyester or with a dibasic acid or with a hydroxy acid or with an aliphatic diacid in the event a carbonate copolymer rather than a homopolymer is desired for use. Polyarylates and polyester-carbonate resins or their blends can also be employed. Branched polycarbonates are also useful, as well as blends of linear polycarbonate and a branched polycarbonate. The branched polycarbonates may be prepared by adding a branching agent during polymerization.

These branching agents may comprise polyfunctional organic compounds containing at least three functional groups which may be hydroxyl, carboxyl, carboxylic anhydride, haloformyl and mixtures comprising a of the foregoing. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), trisphenol PA (4(4(1,1-bis (p-hydroxyphenyl)-ethyl) alpha,alpha-dimethyl benzyl)phenol), 4-chloroformyl phthalic anhydride, trimesic acid and benzophenone tetracarboxylic acid, and the like. The branching agents may be added at a level of about 0.05 to about 2.0 weight percent. Branching agents and procedures for making branched polycarbonates are described, for example, in U.S. Pat. Nos. 3,635,895 and 4,001,184. In addition, all types of polycarbonate end groups are herein contemplated.

For example, the substrate polymer may be a polycarbonate based on bisphenol A, in which each of $A^1$ and $A^2$ is p-phenylene and $Y^1$ is isopropylidene, where the number average molecular weight (Mn) of the polycarbonate is about 5,000 atomic mass units (amu) to about 100,000 amu, as measured by gel permeation chromatography. Optionally, the polycarbonate may have a number average molecular weight of about 10,000 amu to about 65,000 amu, or even a number average molecular weight of about 15,000 amu to about 35,000 amu.

The polycarbonate may be produced by a melt process (e.g., activated carbonate melt process such as those described in U.S. Pat. Nos. 5,151,491 and 5,142,018). Polycarbonates produced by a melt process or activated carbonate melt process may contain a significantly higher concentration of Fries product. As used herein, the terms "Fries" and "Fries product" denote a repeating unit in polycarbonate having the formula (V):

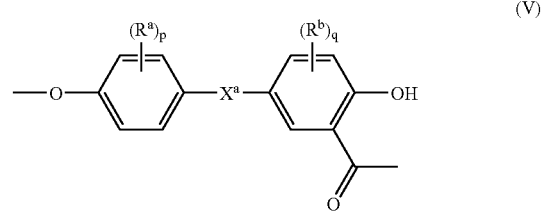

(V)

wherein $X^a$ is a bivalent radical as described in connection with Formula (III) described above. Although the generation of significant Fries product can lead to polymer branching, resulting in uncontrollable melt behavior, such product may be readily identified by a forensic analytical technique. Suitable analytical techniques include, for instance, the proton NMR signal produced by the aromatic protons of the Fries repeat unit or by fluorescence spectroscopy.

Possible polycarbonate compositions may also include various additives ordinarily incorporated in resin compositions of this type. Such additives are, for example, fillers or reinforcing agents; heat stabilizers; antioxidants; light stabilizers; plasticizers; antistatic agents; mold releasing agents; additional resins; blowing agents; and the like, as well as combinations comprising at least one of the foregoing additives. Examples of fillers or reinforcing agents may include glass fibers, asbestos, carbon fibers, silica, talc, calcium carbonate, and the like. Examples of heat stabilizers may include triphenyl phosphite, tris-(2,6-dimethylphenyl) phosphite, tris-(mixed mono- and di-nonylphenyl)phosphite, dimethylbenene phosphonate, trimethyl phosphate, and the like. Examples of antioxidants may include octadecyl-3-(3,5-di-tert-butyl-4-hydroxyphenyl)propionate, pentaerythrityl-tetrakis[3-(3,5-di-tert-butyl-4-hydroxyphenyl) propionate], and the like. Examples of light stabilizers may include 2-(2-hydroxy-5-methylphenyl)benzotriazole, 2-(2-hydroxy-5-tert-octylphenyl)-benzotriazole, 2-hydroxy-4-n-octoxy benzophenone, and the like. Examples of plasticizers may include dioctyl-4,5-epoxy-hexahydrophthalate, tris-(octoxycarbonylethyl)isocyanurate, tristearin, epoxidized soybean oil, and the like. Examples of the antistatic agent may include glycerol monostearate, sodium stearyl sulfonate, sodium dodecylbenzenesulfonate, and the like. Examples of mold releasing agents may include stearyl stearate, beeswax, montan wax, paraffin wax, and the like. Examples of additional resins may include but are not limited to polypropylene, polystyrene, polymethyl methacrylate, polyphenylene oxide, and the like. Combinations of any of the foregoing additives may be used. Such additives may be mixed at a suitable time during the mixing of the components for forming the composition.

In order to be able to authenticate the data storage media, the media, and preferably the polymer (e.g., the substrate), should include an identifier, e.g., a taggant, such as a fluorescent dye, or the like, capable of producing a detectable photoluminescence when excited. Optionally, the polymer may exhibit intrinsic photoluminescence such that it is not necessary to add a taggant in order to produce a detectable photoluminescence. For example, the Fries Product described above may be detected in polycarbonate by use of fluorescence spectroscopy. In another embodiment, a fluorescent monomer is copolymerized into the backbone or endcap of the polymer. Optionally, the media can comprise an optically variable tag, e.g., a compound that has a fluorescence emission that changes in fluorescence intensity and/or wavelength as a function of time. In one embodiment, the media may be designed to be evaluated several times, i.e., the authenticating signal is repeatable, while in other embodiments the authenticating signal may be capable of evaluation only once due to the use of optically variable tags that, for example, degrade after one or more authentication sequences. In one exemplary embodiment, the authenticatable polymer will comprise an optically variable tag that can be authenticated multiple times, i.e., for example, at various points during use in an optical device or kiosk.

Suitable optically variable tags are generally fluorescent or luminescent materials that are selected to be chemically compatible with the polymer and have a heat stability consistent with engineering plastics compounding and in particular with the processing conditions of the portion of the media in which they are included (e.g., the polymer substrate).

Possible optically variable tags include oxadiazole derivatives, luminescent conjugated polymers, and the like. Illustrative examples of suitable luminescent conjugated polymers are blue emitting luminescent polymers, such as poly-paraphenylenevinylene derivatives. Illustrative examples of suitable oxadiazole derivatives include oxadiazole derivatives substituted with a biphenyl or substituted byphenyl in the 2-position and with a phenyl derivative in the 5-position. For example, tert-butyl phenyl oxadiazole, bis(biphenylyl) oxadiazole, as well as mixtures comprising at least one of these tags.

Alternatively, and or in addition, the tag may be a non-optically variable compound. Non-optically variable compounds comprise luminescent tags, and optionally luminescent tags that are selected to enhance the signal from optically variable tags when used in combination. Luminescent tags include an organic fluorophore, an inorganic fluorophore, an organometallic fluorophore, a phosphorescent material, a luminescent material, semiconducting luminescent nanoparticle, and the like, as well as combinations comprising at least one of the foregoing tags.

In an exemplary embodiment, the luminescent tags are selected from classes of dyes that exhibit high robustness against ambient environmental conditions and temperature stability of greater than or equal to about 350° C., preferably greater than or equal to about 375° C., and more preferably greater than or equal to about 400° C. It is desirable to have optically variable tags and/or luminescent tags hidden behind the matrix absorption. The matrix is defined herein as the backbone absorption from the media (e.g., in the substrate) or from any additive or colorant present in the substrate. Alternatively, it is desirable to have optically variable tags and/or luminescent tags with a peak excitation wavelength outside the visible (e.g. in the ultraviolet range) and a peak emission in the visible or in the near infrared region of the spectrum. When the difference between the excitation and the emission peak is greater than about 50 nm, these compounds are usually referred to as long (positive) stokes shift dyes. In an exemplary embodiment, the luminescent tags are selected from the classes of long stokes shift dyes that are excited by long ultraviolet wavelengths and emit in the visible.

Illustrative luminescent tags include fluorescent tags for example, dyes such as polyazaindacenes and/or coumarins (including those set forth in U.S. Pat. No. 5,573,909); lanthanide complexes, hydrocarbon and substituted hydrocarbon dyes; polycyclic aromatic hydrocarbons; scintillation dyes (e.g., oxazoles and oxadiazoles); aryl- and heteroaryl-substituted polyolefins (C2–C8 olefin portion); carbocyanine dyes; phthalocyanine dyes and pigments; oxazine dyes; carbostyryl dyes; porphyrin dyes; acridine dyes; anthraquinone dyes; anthrapyridone dyes; naphtalimide dyes; benzimidazole derivatives; arylmethane dyes; azo dyes; diazonium dyes; nitro dyes; quinone imine dyes; tetrazolium dyes; thiazole dyes; perylene dyes; perinone dyes; bis-benzoxazolylthiophene (BBOT); xanthene and thioxanthene dyes; indigoid and thioindigoid dyes; chromones and flavones derivatives, and the like, as well as combinations comprising at least one of the fluorescent tags disclosed herein. Luminescent tags also include anti-stokes shift dyes that absorb in the near infrared wavelength and emit in the visible wavelength.

The following is a partial list of some fluorescent and/or luminescent dyes: 5-Amino-9-diethyliminobenzo(a)phenoxazonium Perchlorate7-Amino-4-methylcarbostyryl, 7-Amino-4-methylcoumarin, 7-Amino-4-trifluoromethylcoumarin, 3-(2'-Benzimidazolyl)-7-N,N-diethylaminocoumarin, 3-(2'-Benzothiazolyl)-7-diethylaminocoumarin, 2-(4-Biphenylyl)-5-(4-t-butylphenyl)-1,3,4-oxadiazole, 2-(4-Biphenylyl)-5-phenyl-1,3,4-oxadiazole, 2-(4-Biphenyl)-6-phenylbenzoxazole-1,3, 2,5-Bis-(4-biphenylyl)-1,3, 4-oxadiazole, 2,5-Bis-(4-biphenylyl)-oxazole, 4,4'-Bis-(2-butyloctyloxy)-p-quaterphenyl, p-Bis(o-methylstyryl)-benzene, 5,9-Diaminobenzo(a)phenoxazonium Perchlorate, 4-Dicyanomethylene-2-methyl-6-(p-dimethylaminostyryl)-4H-pyran, 1,1'-Diethyl-2,2'-carbocyanine Iodide, 1,1'-Diethyl-4,4'-carbocyanine Iodide, 3,3'-Diethyl-4,4',5,5'-dibenzothiatricarbocyanine Iodide, 1,1'-Diethyl-4,4'-dicarbocyanine Iodide, 1,1'-Diethyl-2,2'-dicarbocyanine Iodide, 3,3'-Diethyl-9,11-neopentylenethiatricarbocyanine Iodide, 1,3'-Diethyl-4,2'-quinolyloxacarbocyanine Iodide, 1,3'-Diethyl-4,2'-quinolylthiacarbocyanine Iodide, 3-Diethylamino-7-diethyliminophenoxazonium Perchlorate, 7-Diethylamino-4-methylcoumarin, 7-Diethylamino-4-trifluoromethylcoumarin, 7-Diethylaminocoumarin, 3,3'-Diethyloxadicarbocyanine Iodide, 3,3'-Diethylthiacarbocyanine Iodide, 3,3'-Diethylthiadicarbocyanine Iodide, 3,3'-Diethylthiatricarbocyanine Iodide, 4,6-Dimethyl-7-ethylaminocoumarin, 2,2'-Dimethyl-p-quaterphenyl, 2,2-Dimethyl-p-terphenyl, 7-Dimethylamino-1-methyl-4-methoxy-8-azaquinolone-2, 7-Dimethylamino-4-methylquinolone-2, 7-Dimethylamino-4-trifluoromethylcoumarin, 2-(4-(4-Dimethylaminophenyl)-1,3-butadienyl)-3-ethylb enzothiazolium Perchlorate, 2-(6-(p-Dimethylaminophenyl)-2,4-neopentylene-1,3,5-hexatrienyl)-3-methylbenzothiazolium Perchlorate, 2-(4-(p-Dimethylaminophenyl)-1,3-butadienyl)-1,3,3-tri methyl-3H-indolium Perchlorate, 3,3'-Dimethyloxatricarbocyanine Iodide, 2,5-Diphenylfuran, 2,5-Diphenyloxazole, 4,4'-Diphenylstilbene, 1-Ethyl-4-(4-(p-Dimethylaminophenyl)-1,3-butadienyl)-pyridinium Perchlorate, 1-Ethyl-2-(4-(p-Dimethylaminophenyl)-1,3-butadienyl)-pyridinium Perchlorate, 1-Ethyl-4-(4-(p-Dimethylaminophenyl)-1,3-butadienyl)-quinolium Perchlorate, 3-Ethylamino-7-ethylimino-2,8-dimethylphenoxazin-5-i um Perchlorate, 9-Ethylamino-5-ethylamino-10-methyl-5H-benzo(a)phe noxazonium Perchlorate, 7-Ethylamino-6-methyl-4-trifluoromethylcoumarin, 7-Ethylamino-4-trifluoromethylcoumarin, 1,1',3,3,3',3'-Hexamethyl-4,4',5,5'-dibenzo-2,2'-indotric arboccyanine Iodide, 1,1',3,3,3',3'-Hexamethylindodicarbocyanine Iodide, 1,1',3,3,3',3'-Hexamethylindotricarbocyanine Iodide, 2-Methyl-5-t-butyl-p-quaterphenyl, N-Methyl-4-trifluoromethylpiperidino-<3,2-g>coumarin, 3-(2'-N-Methylbenzimidazolyl)-7-N,N-diethylaminocoumarin, 2-(1-Naphthyl)-5-phenyloxazole, 2,2'-p-Phenylen-bis(5-phenyloxazole), 3,5,3'''',5''''-Tetra-t-butyl-p-sexiphenyl, 3,5,3'''',5''''-Tetra-t-butyl-p-quinquephenyl, 2,3,5,6-1H,4H-Tetrahydro-9-acetylquinolizino-<9,9a,1-gh>coumarin, 2,3,5,6-1H,4H-Tetrahydro-9-carboethoxyquinolizino-<9,9a, 1-gh>coumarin, 2,3,5,6-1H,4H-Tetrahydro-8-methylquinolizino-<9,9a, 1-gh>coumarin, 2,3,5,6-1H,4H-Tetrahydro-9-(3-pyridyl)-quinolizino-<9, 9a,1-gh>coumarin, 2,3,5,6-1H,4H-Tetrahydro-8-trifluoromethylquinolizino-<9,9a,1-gh>coumarin, 2,3,5,6-1H,4H-Tetrahydroquinolizino-<9,9a,1-gh>coumarin, 3,3',2'',3''''-Tetramethyl-p-quaterphenyl, 2,5,2'''',5''''-Tetramethyl-p-quinquephenyl, P-terphenyl, P-quaterphenyl, Nile Red, Rhodamine 700, Oxazine 750, Rhodamine 800, IR 125, IR 144, IR 140, IR 132, IR 26, IR5, Diphenylhexatriene, Diphenylbutadiene, Tetraphenylbutadiene, Naphthalene, Anthracene, 9,10-diphenylanthracene, Pyrene, Chrysene, Rubrene, Coronene, Phenanthrene; and the like.

Luminescent tags may include luminescent nanoparticles having a size (measured along a major diameter) of about 1 nanometer (nm) to about 50 nanometers. Exemplary luminescent nanoparticles include rare earth aluminates (such as strontium aluminates doped with europium and dysprosium, and the like); semi-conducting nanoparticles (such as CdS, ZnS, $Cd_3P_2$, PbS, and the like); and the like as well as combinations comprising at least one of the foregoing. In one embodiment, fluorescent tags such as perylenes such as Anthra[2,1,9-def:6,5,10-d'e'f']diisoquinoline-1,3,8,10(2H, 9H)-tetrone, 2,9-bis[2,6-bis(1-methyethyl)phenyl]-5,6, 12, 13-tetraphenoxy are utilized as the luminescent tags.

The concentration of the luminescent tags depends on the quantum efficiency of the tag, excitation and emission wavelengths, and employed detection techniques, and will generally be present in an amount of about $10^{-18}$ percent by weight to about 2 percent by weight of the substrate (or layer in which the tag is present), optionally in an amount of about $10^{-15}$ percent by weight to about 0.5 percent, and typically in an amount of about $10^{-12}$ percent by weight to about 0.05 percent by weight.

To further enhance authentication, the polymer compositions may also contain colorants. These colorants may, for example, impart a specific appearance to the tagged polymer or tagged data storage media under normal lighting conditions (e.g., daylight). To enable facile and accurate authentication of the storage media, it is desirable that any colorants used do not interfere with the photoluminescent emissions. For example, the colorant could exhibit no or only very weak fluorescence under UV excitation compared to the taggant (e.g., fluorescent dye). Suitable colorants may include non-fluorescent derivatives of the following dye families: anthraquinones, methine, perinones, azo, anthrapyridones, quinophtalones, and the like, as well as combinations comprising at least one of the foregoing colorants.

It is noted that the above media compositions as well as taggants and optical identifiers are merely exemplary. The disclosed devices and systems can detect various taggants and/or identifiers on various articles.

The authentication system may comprise multiple devices for receiving the property of the energy (e.g., the emissions, (such as, photoluminescent emissions), analog responses, and/or the like). These devices can include light sensing devices such as photodiodes (e.g., optically filtered photodiodes, RGB (red-green-blue) photodiodes, and the like), photovoltaic photodetectors, photoconductive photodetectors, photomultiplier tubes, charge coupled devices (CCD), light to frequency converters, and the like, as well as combinations comprising at least one of these light sensing devices.

In addition the light sensing device may be a filtered photodetector (e.g., filtered with a bandpass filter), such that emissions are detected at a particular wavelength, wherein the desired wavelength is based upon the particular tag (e.g., optical identifier) to be detected. Any suitable bandpass filter may be used, with the bandwidth chosen dependent upon the desired accuracy and type of light sensing device. For example, the filter can be a 10 nanometer (nm) bandpass filter (e.g., a filter that received emissions only in a bandwidth of 10 nm (e.g., from 480 nm to 490 nm, or 550 nm to 560 nm, etc.), 20 nm bandpass filter, 30 nm bandpass filter, 40 nm bandpass filter, 60 nm bandpass filter, or the like.

The number of light sensing devices employed should be sufficient to identify a desired luminescent tag. Generally, greater than or equal to three light sensing devices are desired (e.g., greater than or equal to three optically filtered photodiodes), specifically, greater than or equal to four light sensing devices, more specifically, greater than or equal to eight light sensing devices, and even more specifically, greater than or equal to ten photodiodes, wherein the light sensing devices can be a combination of filtered and unfiltered, with greater than or equal to about three optically filtered light sensing devices desirable. The upper limit on the number of light sensing devices is based upon space limitations and cost, while the lower limit is based upon a sufficient number to obtain the desired identification capability and/or desired accuracy. Optionally, redundant light sensing devices and/or sources may be employed in order to improve authentication reliability and/or to reduce/avoid maintenance for the lifetime of the authentication device.

In one embodiment, the authentication system comprises three optically filtered light sensing devices (e.g., optically filtered photodiodes) that optionally allow for RGB color determination. These optically filtered light sensing devices are capable of detecting analog emission intensity in a spectral sensitivity range with each light sensing device having a different device spectral sensitivity range which includes at least a portion of (and is preferably within) the visible multi-wavelength spectral distribution of one of the light sources. Additionally, the device spectral sensitivity range of at least one (preferably at least two, and more preferably at least tree) of the light sensing devices is disposed in at least a portion of the photoluminescent emission wavelength range of the optical identifier (e.g., the luminescent tag). In other words, if the optical identifier photoluminescent emission wavelength range is 400 nm to 500 nm, the first light sensing device can have a spectral sensitivity range of 380 nm to 425 nm, the second light sensing device can have a spectral sensitivity range of 450 nm to 480 nm, and the third light sensing device can have a spectral sensitivity range of 475 nm to 510 nm. In an alternative cx anplary system, if the optical identifier photoluminescent emission wavelength range is 400 nm to 500 nm, the first light sensing device can have a spectral sensitivity range of 400 nm to 425 nm, the second light sensing device can have a spectral sensitivity range of 435 nm to 455 nm, and the third light sensing device can have a spectral sensitivity range of 475 nm to 510 nm. In yet another embodiment where the optical identifier photoluminescent emission wavelength range is 400 nm to 500 nm, with a peak emission wavelength of 475 nm, the first light sensing device can have a spectral sensitivity range of 400 nm to 425 nm, the second light sensing device can have a spectral sensitivity range of 435 nm to 455 nm, and the third light sensing device can have a spectral sensitivity range of 460 nm to 475 nm. Optionally, additional light sensing device(s) having a spectral sensitivity range greater than the peak emission wavelength can also be employed. In other words, a first photodiode can have a first peak in a first wavelength range where the photoluminescent emission is at 10% to 70% of a maximum photoluminescence intensity, a second photodiode can have a second peak in a second wavelength range where the photoluminescent emission is at 10% to 70% of the maximum photoluminescence intensity; and a third photodiode has a third peak in a third wavelength range where the photoluminescent emission is at 70% to 100% of the maximum photoluminescence intensity.

In one embodiment, the first light sensing device is a green filtered photodiode, the second light sensing device is a blue filtered photodiode, and the third light sensing device is a red filtered photodiode. Optionally, in addition to the filtered light sensing devices, a light sensing device that is not filtered (i.e., unfiltered) in the visible multiwavelength spectral distribution of one of the light sources may be used. Note that the term "unfiltered" light sensing device refers to the absence of selective wavelength filtration in the visible range. The "unfiltered" light sensing device may include window or filter to block ultraviolet or near infrared wavelengths that could interfere with the detection of the analog signature.

FIG. 1 is a top view schematic illustration of one embodiment of an authentication device comprising multiple light sources and light-sensing devices that would operate in reflectance mode. This figure shows the light sensing devices (photodiode "PD"; PD1, PD2, PD3, and PD4), disposed adjacent the light sources, (LED1, LED2, LED3, and LED4), and a filtered photodiode array "U2".

The spectral sensitivity range of each of the various light sensing devices is desirably different (although redundancy in the system is also contemplated). One or more of the light sensing devices can have a narrow device spectral sensitivity bandwidth (i.e., less than or equal to 60 nm); for example, 5 nm to 60 nm, or peak ± less than or equal to 30 nm. Specifically, a combination of the light sensing devices desirably covers the wavelengths of 360 nm to 780 nm, with coverage of the wavelengths of 380 nm to 750 nm acceptable, and coverage of 400 nm to 700 nm more practical while allowing good color determination. For example, a photodiode can have a spectral sensitivity range and have a peak that corresponds to a shortest wavelength of the desired photoluminescent emission wavelength range ±5 nm, and another photodiode can have a spectral sensitivity range and have a peak that corresponds to a longest wavelength of the desired photoluminescent emission wavelength range ±5 nm.

The light sensing device(s) may have a device spectral sensitivity bandwidth of less than or equal to 40 nm, specifically a device spectral sensitivity bandwidth of less than or equal to 20 nm, and more specifically a device spectral sensitivity bandwidth of less than or equal to 10 nm. Various embodiments of light sensing device combinations comprise 3, 4, 5, 6, 7, 8, 9, or more light sensing devices having a narrow device spectral sensitivity bandwidth, in combination with 0, 1, 2, 3, or more unfiltered light sensing devices (wherein unfiltered is in reference to in the range of the spectral distribution of the multiwavelength light source).

An additional, filtered photodiode may be employed having a fourth peak spectral sensitivity wavelength corresponding to a wavelength at which the photoluminescent emission band has an intensity of less than or equal to about 1% of its peak intensity. For example, the fourth peak spectral wavelength can be a wavelength of less than or equal to ±15 nm of a wavelength where the emission intensity of the luminescent tag became zero (i.e., is no longer detectable). In another example, a photodiode can have a spectral sensitivity range and have a peak that is within 100 nm of a longest wavelength at which the desired photoluminescent emission wavelength range has an intensity of less than 1% of a maximum desired photoluminescence intensity.

In addition or alternative to the fourth filtered photodiode, a clear (i.e., unfiltered) photodiode can be employed. The clear photodiode can detect color across a broad spectrum, e.g., can detect a colorant, the visible portion of the absorption of a CD-R dye, metal effects, a metallic layer (e.g., a reflective layer) and/or "clear/colorless" medium, that is employed in addition to the particular tag (e.g., fluorescent). The clear photodiode typically provides information regarding the total brightness of the photoluminescent emission or the lightness/darkness of the color. It may also be used to verify that the sources are operating properly during an internal calibration or self-checking procedure.

In addition to the photodetectors that receive the emissions, the detector and/or the device in which the detector is employed, comprises two or more sources of energy, e.g., electromagnetic radiation. One source of electromagnetic radiation at least emits radiation in the UV portion of the spectrum, while a second source of electromagnetic radiation at least emits radiation in the visible light portion of the spectrum. Possible electromagnetic radiation sources include light emitting diode(s) (LED) (such as a ultraviolet (UV) and visible light emitting diode(s) and preferably visible light LEDs emitting white light), wherein the light emitting diode may comprise a light emitting diode array. In one embodiment, white light LEDs are defined as the LEDs with a CIE 1931 (Commission Internationale de l'Eclairage) chromaticity x=0.25 to 0.33, and y=0.21 to 0.42.

In addition, the light sensing device may comprise photo multiplier tube(s), charge-transfer device(s) (e.g., a charge-coupled device, intensified charge-transfer device, a charge-injected device, and/or the like), optical probe(s) (e.g., a fiber-optic probe), and/or light guiding element(s). LEDs are generally desirable if the electromagnetic radiation source is provided on the detector due to size, durability, and cost considerations. Wherein the detector can comprise a UV LED (capable of emitting radiation in the UV range of the light spectrum), and non-UV LED (capable of emitting radiation outside the UV range of the light spectrum; e.g., visible light). Optionally, two or more UV LEDs and two or more non-UV LEDs (e.g., visible light or white light LEDs) can be employed in combination.

Figure 2:
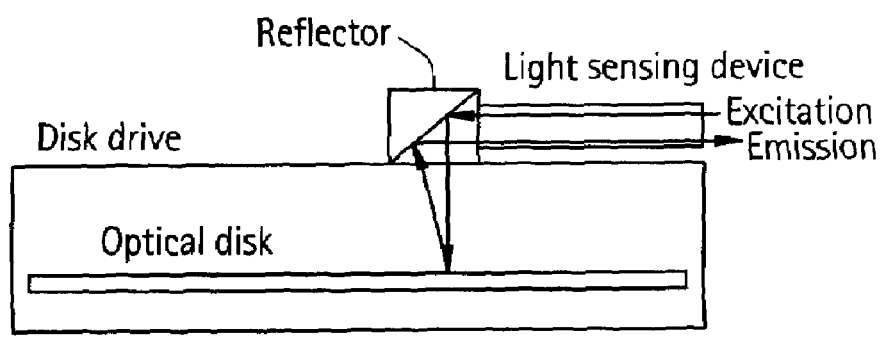
FIG. 2 is a schematic diagram of a possible location of a light sensing device (e.g., fiber-optic probe).
Figure 3:
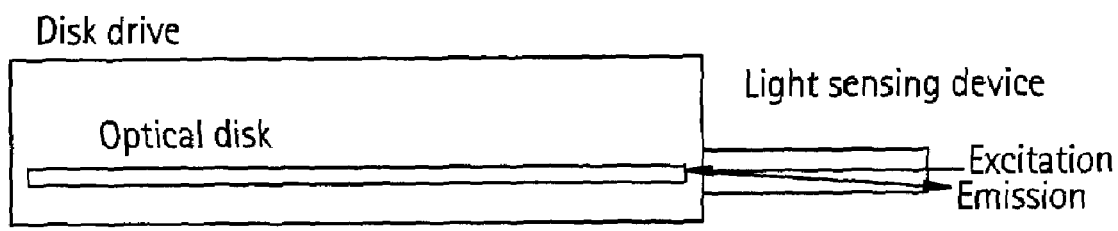
FIG. 3 is another schematic diagram of a possible location of a light sensing device (e.g., fiber-optic probe).

FIGS. 2 and 3 illustrate possible locations of a light sensing device (e.g., fiber-optic probe(s)). Additional arrangements of light sensing devices are possible that take advantage of wave guiding structure of an optical disc. In particular, light can be launched into the disc from the label or read side of the disc while fluorescence and scatter are detected from the edge of the disc. Such configuration provides a capability of reducing the loading of colorimetric and fluorescent reagents into the material of the disc.

The orientation of the filtered photodiode and, optionally the clear photodiode, is dependent upon the number of photodiodes employed as well as the size of the detector (which is preferably less than or equal to about 5 square centimeters), and the ability of the photodiodes to receive the emission from the media. The photodiodes and the electromagnetic radiation sources may be disposed adjacent one another such that a fluorescence wavelength and intensity can be measured in reflectance mode. In one embodiment, electromagnetic radiation sources and the photodiodes can be oriented around the edges of the detector, in an alternating fashion, with a resistor disposed on an interior portion of the detector (e.g., away from the edges; toward and/or in the middle).

In addition to the resistor, electromagnetic radiation sources, and photodiodes, the detector may optionally comprise optical probe(s) or light guiding element(s), temperature sensor(s), an ability to internally calibrate (e.g., a highly reflective white section with or without a reference luminescent tag) and/or to check the integrity of its components, comparator(s), as well as combinations comprising at least one of the foregoing, wherein the calibration can be user initiated and/or automatic. When operating in a normal fashion, the detector may be able to return a pass/fail signal and optionally an error status signal. Note that the comparator unit may include components to perform signal processing tasks such as amplify, filter, and/or convert the analog signal from the light sensing devices to form a detected analog signature that the comparator can directly compare to an authentic analog signature.

Light sources and detectors are positioned at certain angles with respect to the measured article. In particular, color detection is performed when the light source and detector are positioned at similar angles to the surface of the article. (See FIG. 4, where the length "l" may optionally be less than or equal to about 20 millimeters (mm), and the depth "d" between the circuit board and the media may optionally be about 10 mm.) These angles can be 89 to 1 degrees, specifically 80 to 10 degrees, and more specifically, 75 to 15 degrees. Detection of photoluminescence is performed with a light source positioned at an angle to the surface of the article and the detector positioned parallel to the surface with the angle of the light source for photolumination excitation similar to the ranges for color detection.

This detector can be employed in various devices, such as optical devices (e.g., CD/DVD players and/or burners, kiosks (e.g., for disposing (e.g., burning) data onto the media, and the like). The optical device may comprise one or more of the electromagnetic radiation sources used by the detector in the authentication process. When one or more of the electromagnetic radiation sources are not part of the detector, but are part of the optical device, the authenticity may be determined in either a reflectance mode (i.e., by emissions reflected from the media) or a transmission mode (emissions transmitted through the media).

In addition to the electromagnetic radiation source(s), the optical device may comprise the comparator(s), and media receiving portion(s) (e.g., conveying system(s), drive(s), robotic arm(s), medium (e.g., disc) pick-up system(s), and/or the like). Additionally, it is desirable to shield the authentication system from outside light, which could affect the authentication by creating undesirable noise that could limit the performance of the system. Methods to shield the authentication system include having an opaque enclosure (e.g., optical drive enclosure where the authentication is performed only when the tray is closed), using opaque sidings/gaskets for contact measurements (e.g., measurement will be performed when the system is in contact with the medium and the outside light is blocked by the gasket).

Figure 5:
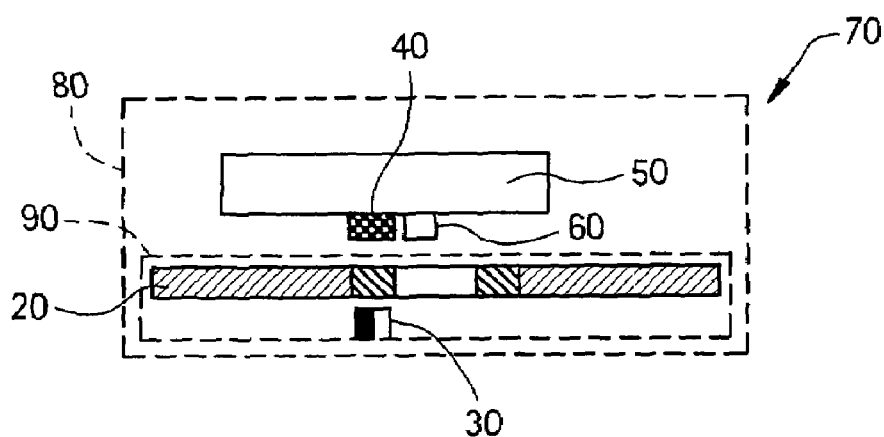
FIG. 5 is a schematic diagram of one embodiment of an overall configuration for an authentication system.

In FIG. 5, one embodiment of a detector system configuration 70 is shown. The system 70 comprises a tester casing 80 that encloses a disc tray 90, and a circuit board 50. The circuit board 50 comprises a filtered photodiode array 40 and a temperature sensor 60, while the disc tray 90 encloses a recordable compact disc drive 20 and electromagnetic sources 30 (e.g., UV LED(s) and white LED(s)).

Figure 6:
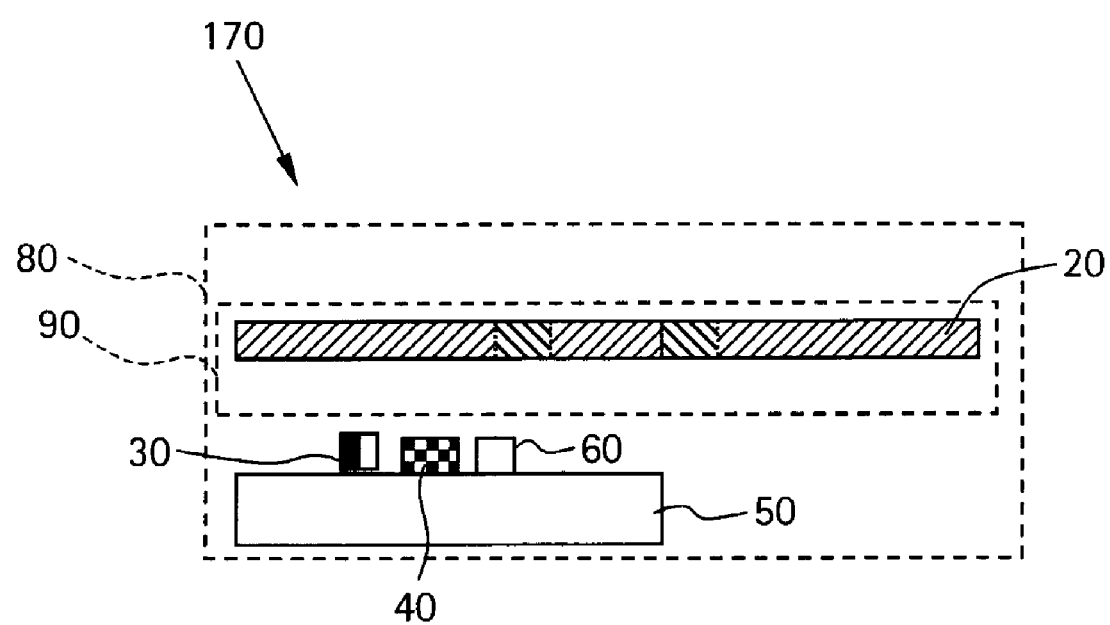
FIG. 6 is a schematic diagram of another embodiment of an overall configuration for the authentication system.

In FIG. 6, another embodiment of a detector system configuration 100 is shown. The system 170 comprises a tester casing 80 that encloses a disc tray 90, and a circuit board 50. The circuit board 50 comprises a filtered photodiode array 40 and a temperature sensor 60, while the disc tray 90 encloses a recordable compact disc 20 and electromagnetic sources 30 (e.g., UV LED(s) and white LED(s)).

In order for the detector to be practical for use in a kiosk and/or in a CD/DVD player or burner, the size of the detector is preferably sufficiently small (e.g., less than or equal to about 8 square centimeters). Preferably the size is less than or equal to about 5 square centimeters.

Use of the detector in an optical device enables the authentication of the medium disposed in the device. By authenticating the medium, a determination can be made whether data (e.g., digital content) should be disposed onto the medium (e.g., if the medium is authentic, data can be disposed on or read from the medium, while if it is not authentic, the device can reject the medium, and data is not read from or written to the medium). Optionally, data will be selected from a digital content library where the content is typically transferred to a recordable disc (e.g. DVD-R, CD-R, and the like). Data could be in a compressed (e.g. MP3, MPEG-2, JPEG, and the like) or noncompressed format.

Figure 7:
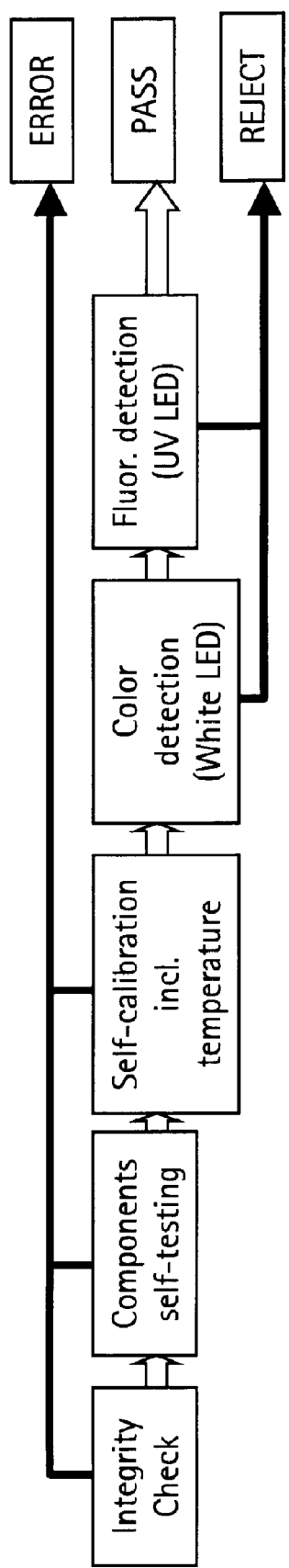
FIG. 7 is a flow chart diagram of one embodiment of a method of using the authentication system in a kiosk machine.

For example, the method of authenticating a data storage medium can include providing a user with authentic medium (e.g., selling authentic media to a user). Once a medium is disposed in the optical device, it is authenticated (e.g., to ensure it was properly purchased . . . ). FIG. 7 illustrates one possible method for controlling the operation of the kiosk machine based on the detection of color and/or fluorescence contained on media, e.g., on a CD-R disc. During the detection, the radiation sources emit radiation that causes an authentic media to produce a photoluminescent emission at a predetermined wavelength/wavelength range. The filtered photodiodes detect the emission and provide a signal to the comparator (e.g., the intensity of the emission at the particular filtered photodiode's peak spectral sensitivity wavelength). The comparator (e.g., computer, microprocessor, logic circuit board, or the like) can compare the received signals with the expected signals to determine if the media is authentic. If the media is not authentic, the comparator can inhibit the optical device from reading from and/or writing (e.g., user selected digital content) to the media.

The comparator can operate, for example, using a preexisting value of color emission and/or fluorescence emission preprogrammed into the computer and that is compared to the value of emissions obtained from the user provided data storage medium being authenticated. Alternatively, the obtained value of color emission and/or fluorescence emission can be compared to pre-established color and fluorescence values obtained by reading a color and/or fluorescence authentication code readable from the user provided data storage medium. Optionally, the authentication can include confirming the presence of a digital security identifier (serial number or code mastered on the disc, pattern of errors, digital watermark, special identifier in the table of content, special digital code in the lead-in region of the disc, sectors or clusters of data which undergo a state change when exposed to the drive laser, and the like).

For example, authentication can comprise illuminating a tested medium with a first light source to produce a tested photoluminescent emission, illuminating the tested medium with a second light source in the visible wavelength range to produce a second analog response, wherein the second analog response is different from the tested photoluminescent emission. A first intensity of the tested photoluminescent emission can be determined, wherein the first intensity is determined in a first wavelength range that includes the desired photoluminescence peak intensity. A second intensity of the tested photoluminescent emission can be determined, wherein the second intensity is determined in a second wavelength range, and a third intensity of the tested photoluminescent emission can be determined. The third intensity is determined in a third wavelength range. The first, second, and third wavelength ranges are different. The comparator can then determine if the first intensity, the second intensity, and the third intensity of the tested photoluminescent emission correspond to the optical photoluminescence identifier (e.g., the fluorescent tag); and if a second analog signal response corresponds to a color identifier, the tested medium is authenticated as the authentic medium.

Optionally, the second analog response can be authenticated by determining a first response intensity, second response intensity, and third response intensity of the second analog response (all at different wavelengths). If the first intensity, the second intensity, and the third intensity of the tested photoluminescent emission correspond to the optical photoluminescence identifier (e.g., the fluorescent tag); and if the first response intensity, the second response intensity, and the third response intensity correspond to the color identifier (e.g., the color), the tested medium is authenticated as the authentic medium. It is noted that the number of intensities determined relating to the photoluminescent emission and the number of response intensities determined relating to the second analog signal is merely dependent upon the number of light sensing devices employed.

Figure 8:
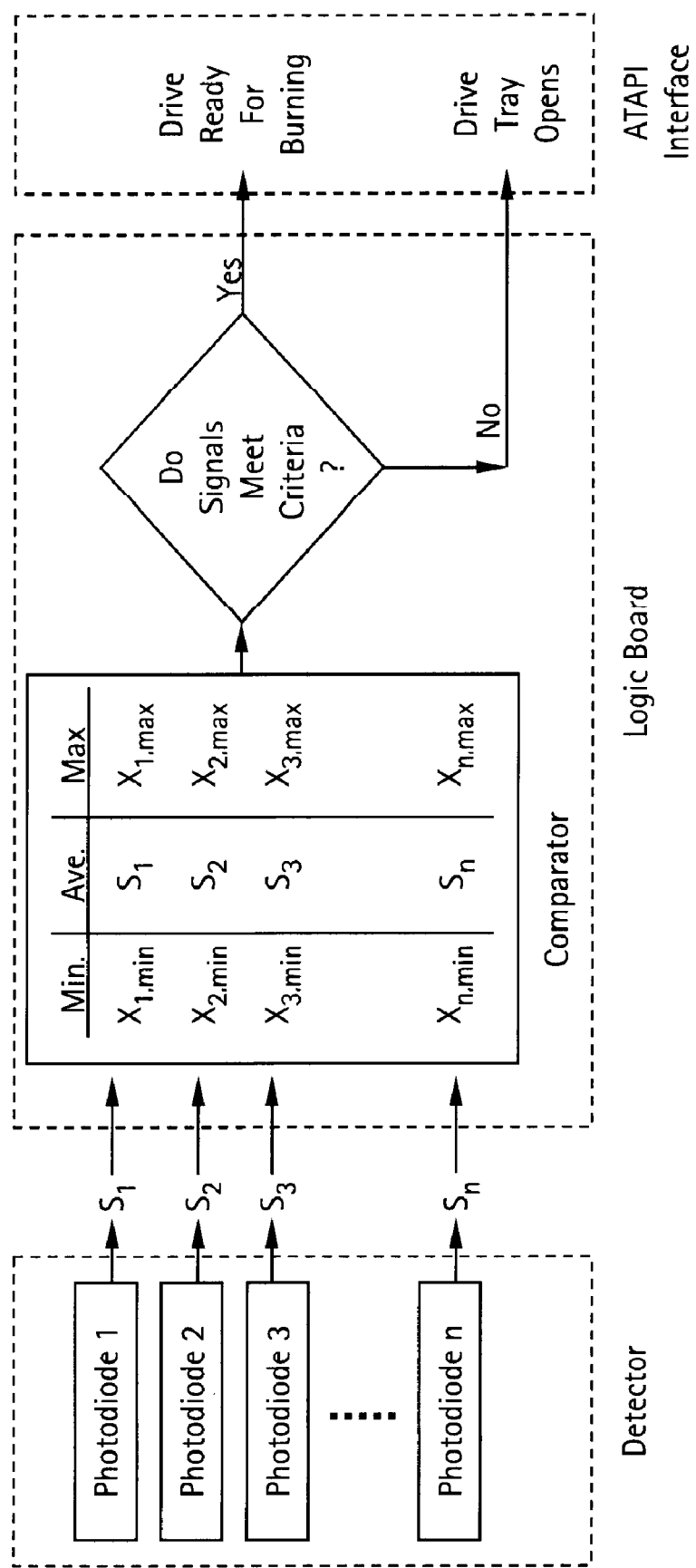
FIG. 8 is a flow chart diagram of one embodiment of a method for authenticating a data storage medium based on signals from multiple photodiodes of the authentication system in a kiosk machine.

Referring to FIG. 8, an authentication scheme for authentication of a media in a media drive (e.g., a CD-R in a kiosk or a DVD in a DVD player) is illustrated. The multiple photodiodes in the detector each detect a signal ($S_1$, $S_2$ . . . $S_n$). The detected signal is compared to a predetermined range (upper limit $X_{1,max}$, $X_{2,max}$, . . . $X_{n,max}$, respectively; and lower limit $X_{1,min}$, $X_{2,min}$, $X_{n,min}$, respectively). If the detected signals meet are authentic (i.e., $X_{1,max} \geq S_1 \geq X_{1,min}$; $X_{2,max} \geq S_2 \geq X_{2,min}$ . . . , and $X_{n,max} \geq S \geq_{n,min}$), the drive is ready for burning/reading . . . However, if the media is not authentic (i.e., $X_{1,max} \leq S_1$, $S_1 \leq X_{1,min}$, $X_{2,max} \leq S_2$, $S_2 < X_{2,min}$, . . . $X_{n,max} \leq S_n$, and/or $S_n \leq X_{n,min}$), the drive tray will open without reading or writing to the media. Alternatively, or in addition to, an error signal could be sent via the drive interface to the kiosk to otherwise prevent writing of data to the non-authentic disc. It is noted that the ranges can be established in any desired fashion, e.g., the endpoints can be inclusive or exclusive (or a combination thereof for the different signals), a media can be rejected if it fails to meet one signal criteria, or can fail only after more than one criteria have been failed. Additionally, this type of system can be part of a new media system or can be an upgrade for a current media system. The logic can be fixed or can be changeable (e.g., upgradeable), depending on the requirements and uses for the particular media authentication device. Finally, multiple logics can be employed in a device to enable it to authenticate a number of different media.

For example, the detection of the color emission and/or fluorescence emission from a data storage medium containing the optical identifier may comprise exposing the user provided data storage media to light from the label and/or read side of the data storage media and collecting and analyzing fluorescence and scatter which are detected from a side or an edge of the user provided data storage media. When the user provided data storage medium containing the optical identifier is authenticated, only then will the kiosk computer allow for the recordation of the user selected digital content onto the data storage media provided to the kiosk machine by the user of the kiosk machine. Preferably the kiosk machine may be contained in a tamper-proof structure to prevent alteration of the kiosk computer or other kiosk machine components.

In addition to the tag(s), the data storage medium which is authenticated and data is disposed thereon, may have additionally recorded thereon identifying information about the user and the digital kiosk machine in which the digital content was recorded (e.g., to make the media traceable). Some non-limiting examples of identifying information which may be additionally recorded onto the data storage medium may be the user's name, credit card information, time and date of recording, amount charged for the recording, additional security features which render the data storage medium copy-proof, and the like.

EXAMPLE 1

Figure 9:
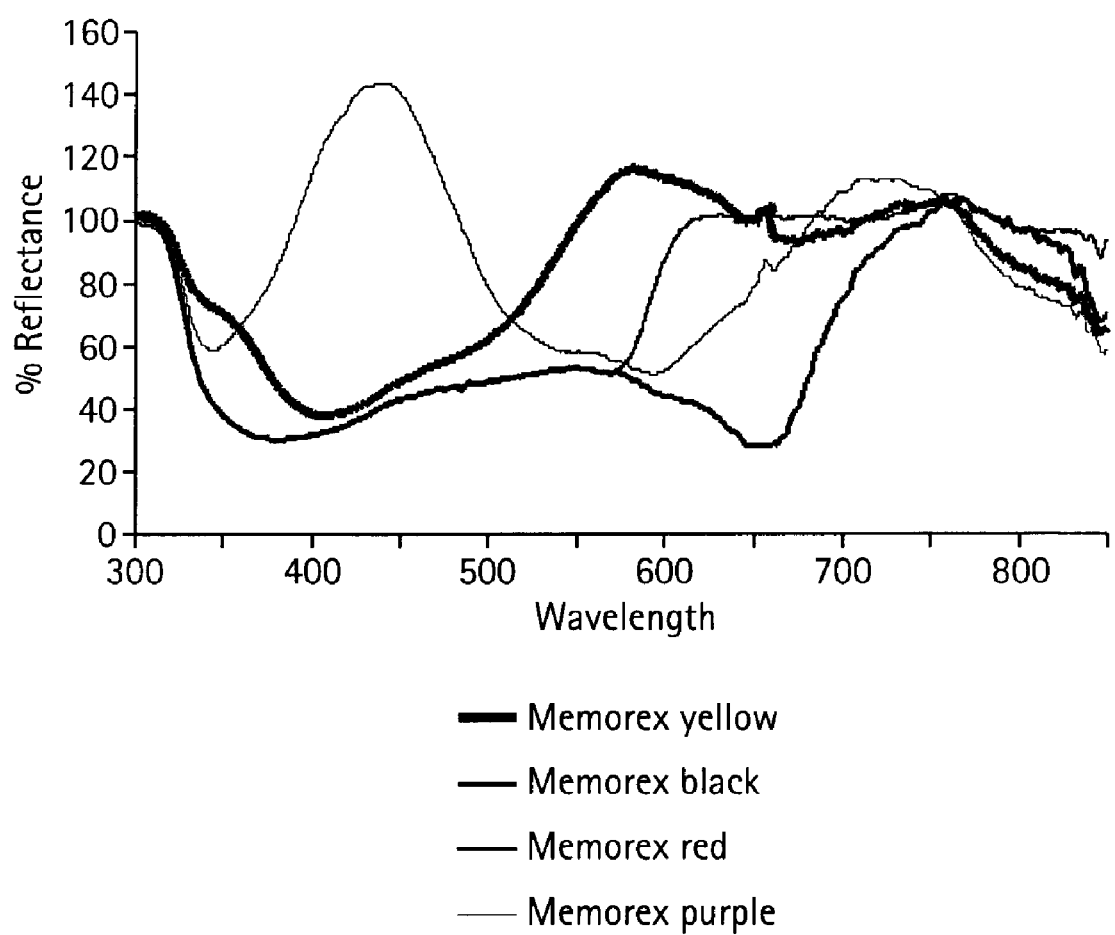
FIG. 9 is a graphical representation of the reflectance spectra of several different colored CD-R discs.

A variety of CD-Rs with different colors were measured with an Ocean Optics reflectance spectrophotometer. FIG. 9 indicates that the reflectance spectra varies depending on the color of the CD-R. Among those CD-Rs measured were Memorex "Cool Colors" (yellow, black, red, and purple). As can be seen from the graph, different colors provide different spectral features.

EXAMPLE 2

A variety of CD-Rs with different colors were measured with a Texas Advanced Optoelectronics Systems Model TCS230EVM Color Sensor Evaluation Module utilizing one white light emitting diode and an RGB sensor. Table 1 indicates that the measured intensity of the filtered photodiodes varies depending on the color of the CD-R. Among those CD-Rs measured were Memorex "Cool Colors" (yellow, black, red, and purple). As can be seen from Table 1, different colors provide different reflected intensities (in arbitrary units). Reflected intensities from a white calibration standard (a white label on the label-side of a CD-R and a colorless CD-R were also measured as a comparison.

TABLE 1

| Sample | Photodiode Intensity (a.u.) | | |
|---|---|---|---|
| Color Measurements | Red | Green | Blue |
| White Reference (note: white label on label-side of CD) | 4070 | 4090 | 4067 |
| Colorless CD-R | 2778 | 3279 | 3125 |
| Memorex Yellow CD-R | 2725 | 2093 | 856 |
| Memorex Red CD-R | 2612 | 838 | 597 |
| Memorex Purple CD-R | 1537 | 807 | 1653 |
| Memorex Blue CD-R | 1188 | 1149 | 2301 |
| Memorex Black CD-R | 900 | 608 | 557 |

EXAMPLE 3

Figure 10:
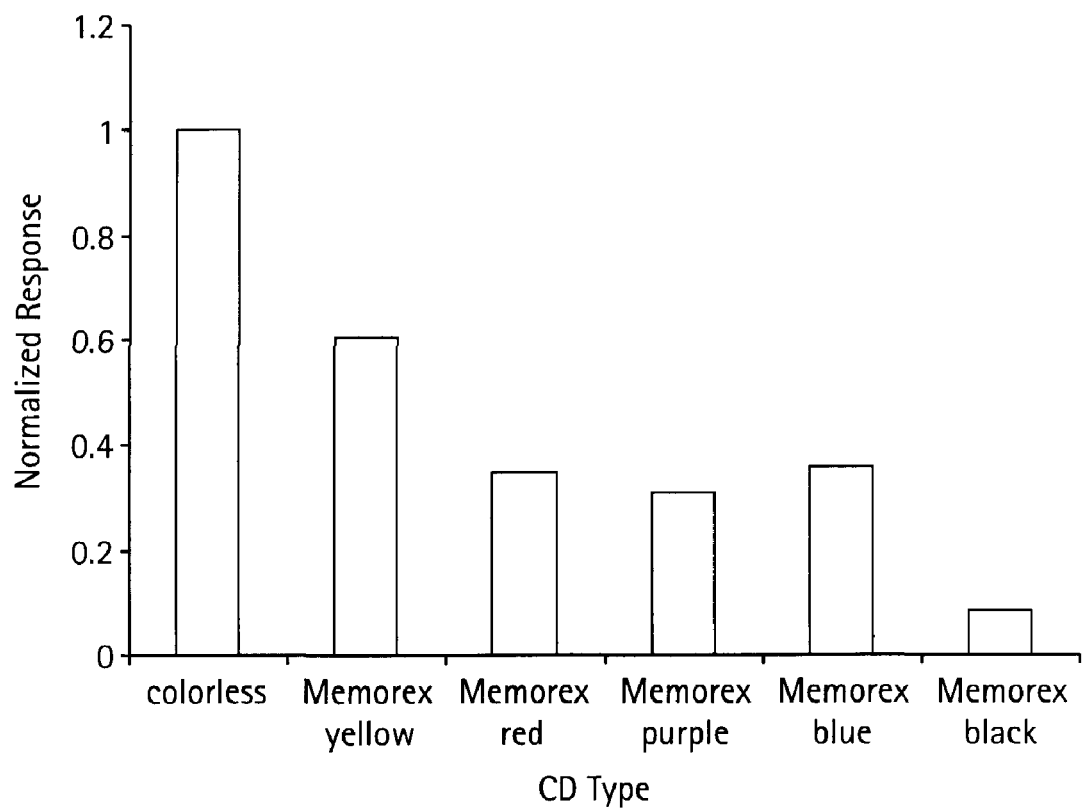
FIG. 10 is a graphical representation of the normalized response of several different colored CD-R discs using a white light LED with no filters.

A variety of CD-Rs with different colors were measured with an in-house detector comprising of a white light, light emitting diode (LED) and a photoconductive silicon photodiode. The LED and photodetector were arranged so that the light was measured in reflectance mode (e.g., such as with the device illustrated in FIG. 4). FIG. 10 shows the detector response normalized to the detector response of the colorless CD-R for several colored CD-Rs. The figure indicates that the detector is capable of discriminating between various colors.

EXAMPLE 4

Figure 11:
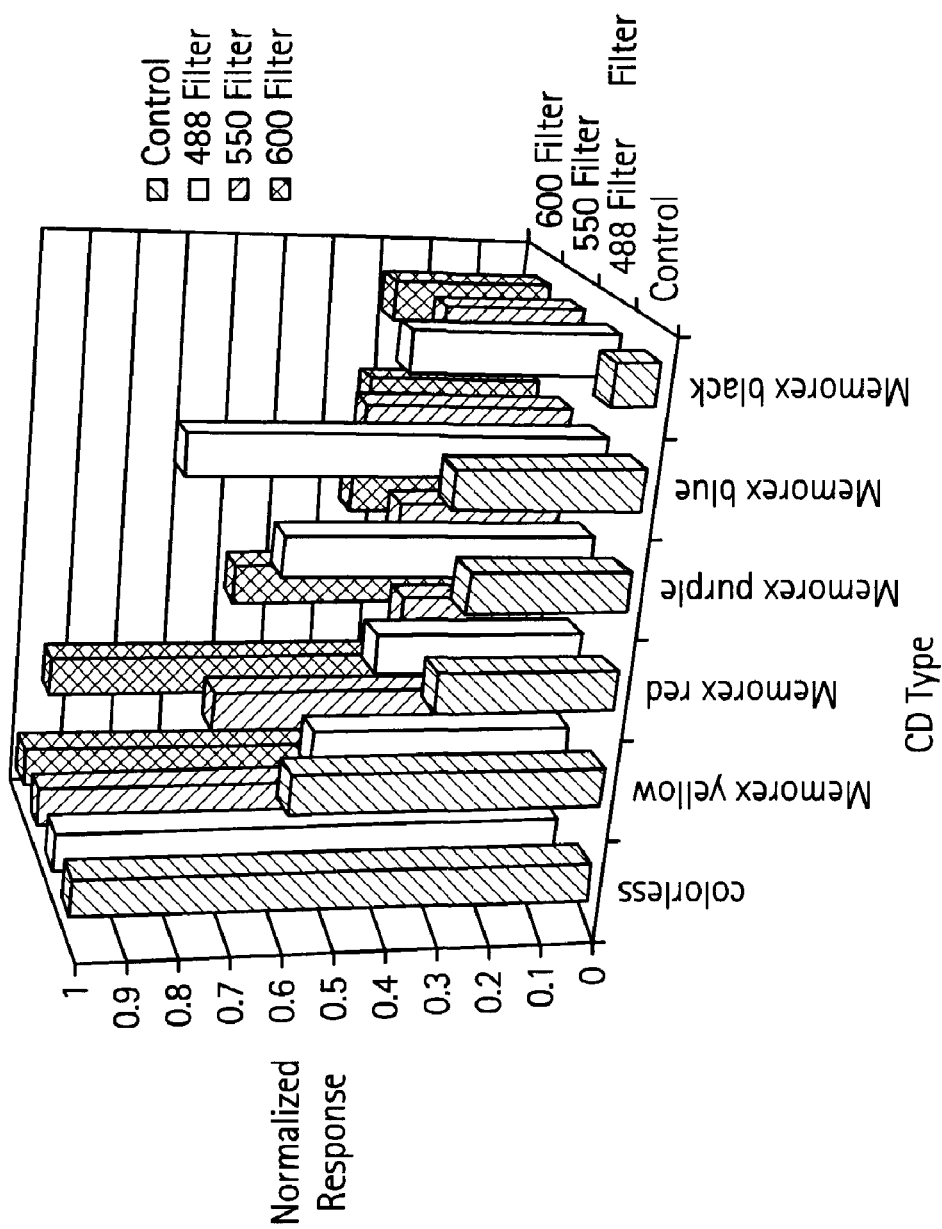
FIG. 11 is a graphical representation of the normalized response of several different colored CD-R discs comparing the effect of using filtered and non-filtered photodiodes.
Figure 12:
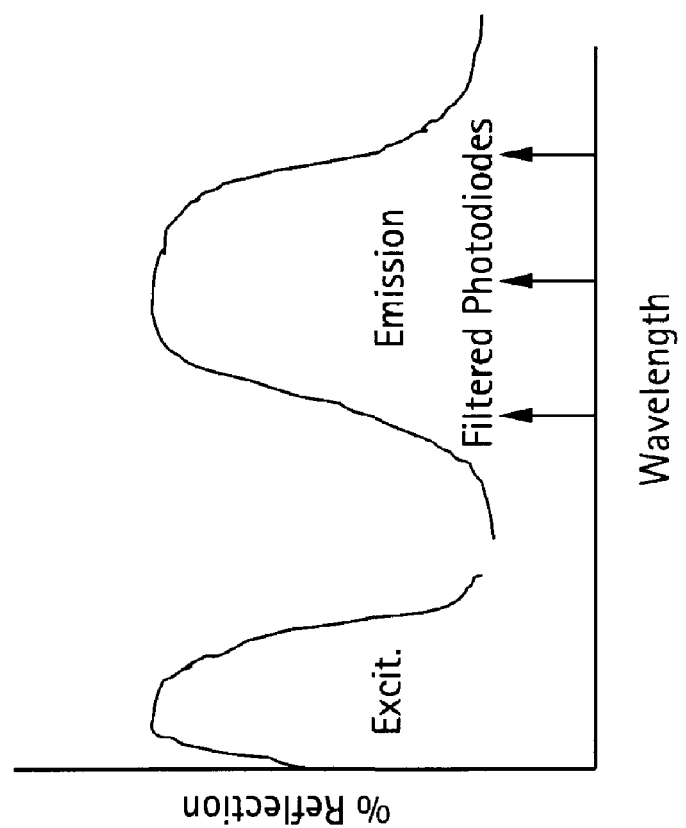
FIG. 12 is a graphical illustration of percent reflection versus wavelength using three filtered photodiodes for color determination.
Figure 13:
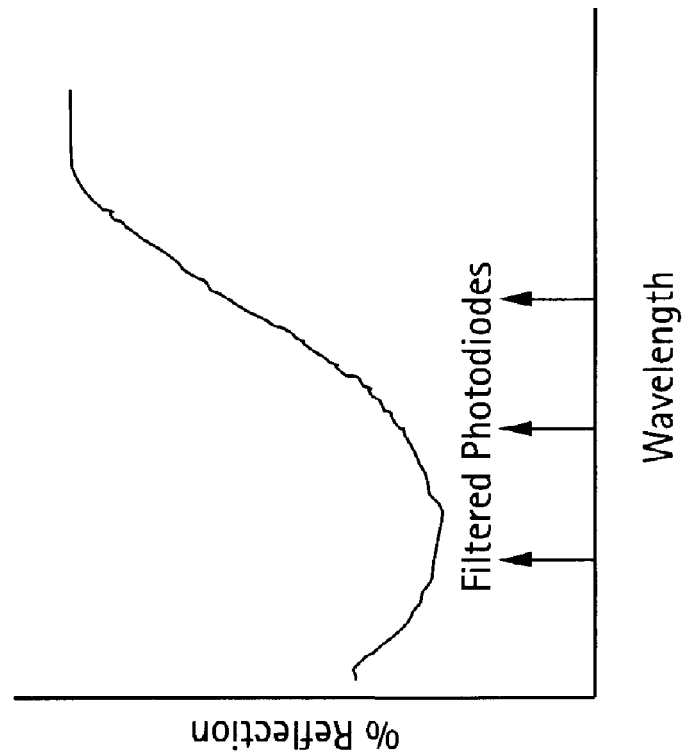
FIG. 13 is a graphical illustration of percent reflection versus wavelength using three filtered photodiodes for fluorescence determination.

The CD-Rs from Example 2 were measured using an in-house detector comprising a white light source, and various silicon photodiode with 10 nm bandpass filters: 488 nm, 550 nm, and 600 nm. The LED and photodetector were arranged so that the light was measured in reflectance mode with light passing through the bandpass filters prior to the photodiode. FIG. 11 shows the normalized detector response for a colorless CD-R and several colored CD-Rs using unfiltered and filtered photodiodes. The figure indicates that the detector is capable of discriminating between various colors with the use of filtered photodiodes. The ability of the detector to discriminate between the colors is enhanced with the use of the filtered photodiodes. FIGS. 12 and 13 illustrate how numerous filtered photodiodes can be employed to detect particular emissions (FIG. 12, color emission; and FIG. 13, fluorescence emission).

EXAMPLE 5

Figure 14:
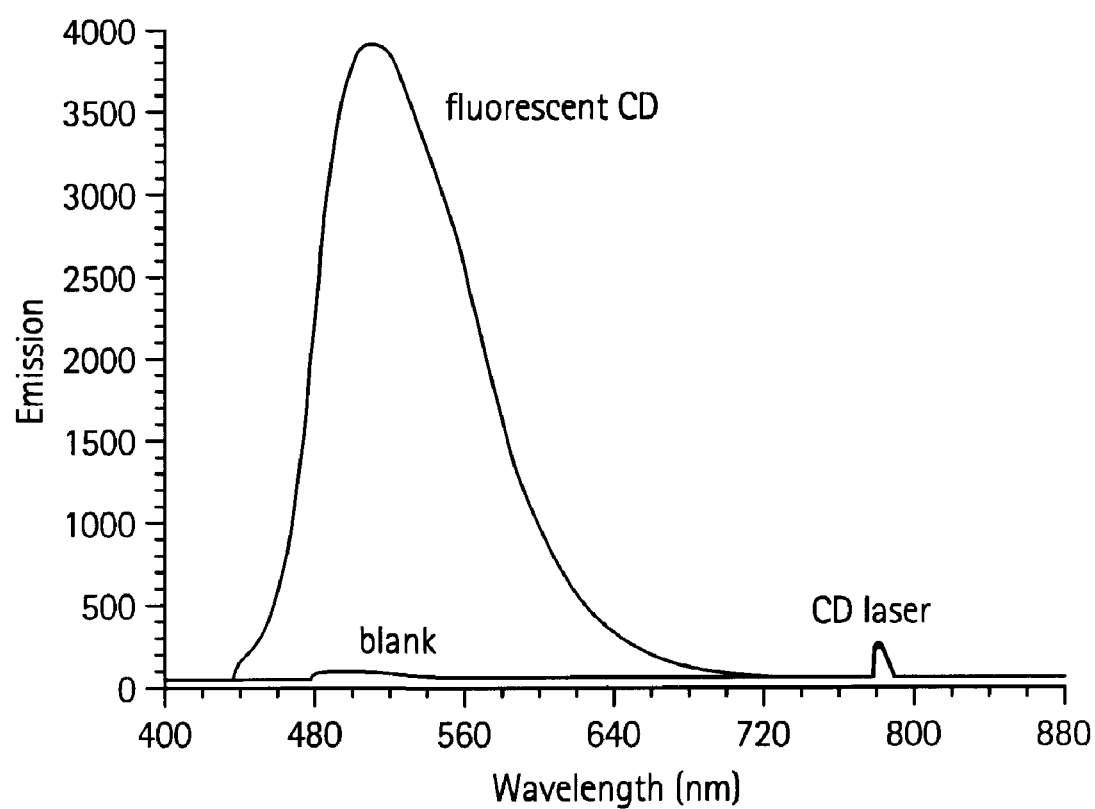
FIG. 14 is a graphical representation of the fluorescence signal obtained from a CD-R disc in a detector drive.

The detector was integrated into a CD-R drive by use of a fiber optic probe. A hole was cut into the outside case of a CD/DVD combo drive. A fiber-optic probe was placed through the hole and used to measure reflectance spectra and fluorescence emission from a CD-R disc placed in the drive. FIG. 14 show the fluorescence signal obtained from the detector in the drive.

EXAMPLE 6

Figure 15:
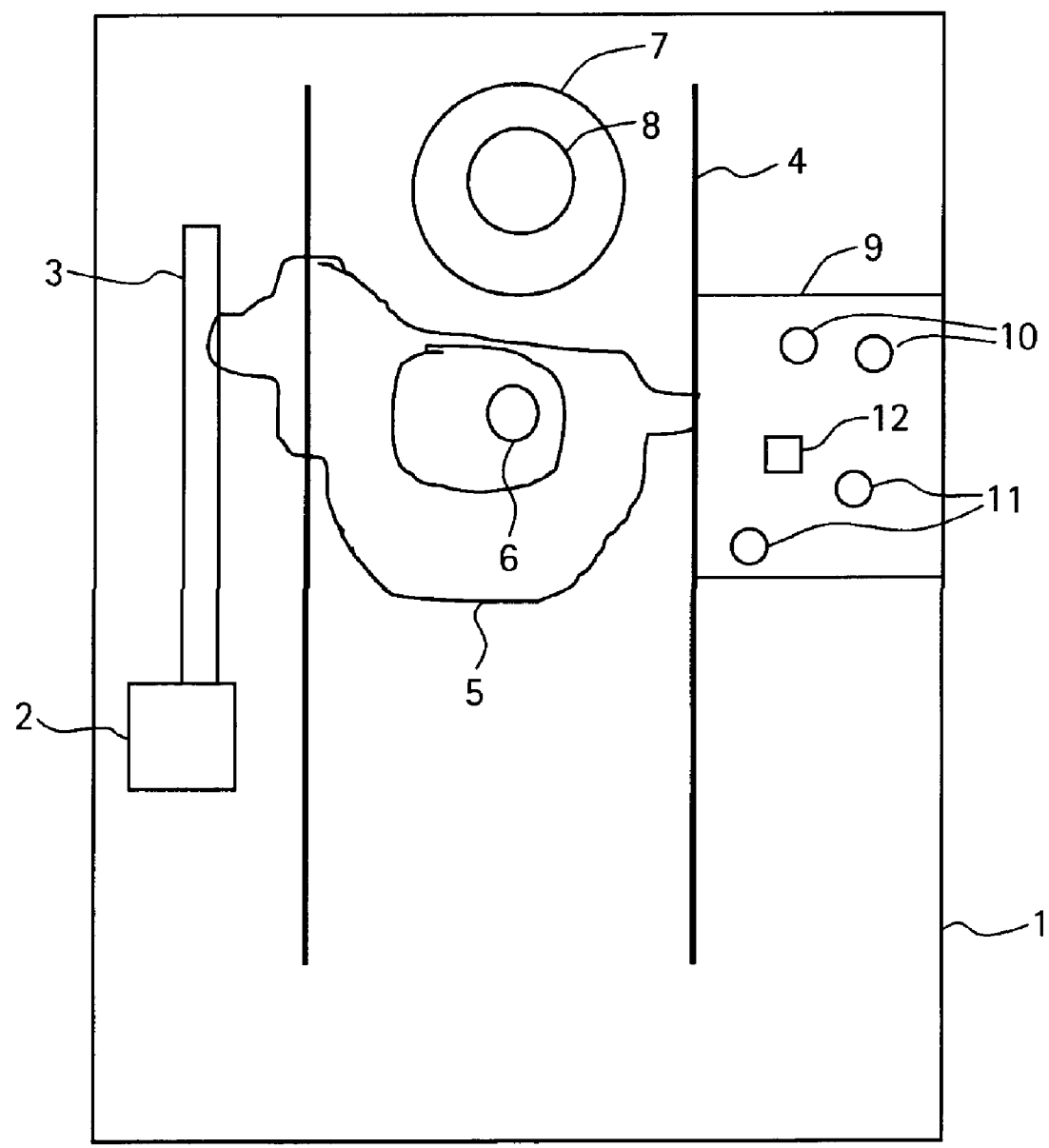
FIG. 15 is a schematic illustration of an internal view of an exemplary embodiment of an optical device including an authentication device.

FIG. 15 is an internal view of an exemplary embodiment of an optical drive modified to include the authentication device. The optical drive includes a carriage 1, tracking motor 2 with a motor screw 3, and a spindle assembly 7 with the spindle 8. The optical pickup assembly 5 has an optical pick up unit 6 that translates on a rail 4. The detector board 9 is disposed adjacent the optical pickup assembly 5. The detector board comprises white LEDs 10, UV LEDs 11, and RGB sensor (filtered photodiode array) 12 and optionally additional filtered photodiodes.

The color and fluorescence of CD-Rs containing a fluorescence taggant was measured using an authentication measurement device in the modified optical drive shown in FIG. 15. Various CD-R discs were placed one at a time into the drive tray of the modified optical drive. The tray was closed and measurements were taken using the detector inside the drive. As Table 2 indicates, the detector has the ability to discriminate discs based on color and on fluorescence (whether the CD-R or CD discs contain or do not contain a fluorescent taggant). In particular, Comparative Example 1, a colored CD-R disc, had a distinctly different reflectance intensity as measured using a white light source with the red, green and blue filtered photodiodes than a white reference (a white label). In addition, Comparative Examples 2 and 3, colored CD discs, had nearly the same measured color-within experimental error-as Comparative Example 1. Meanwhile, Comparative Examples 1 and 2, CD-R and CD discs containing a fluorescent taggant, had similar fluorescence emission characteristics as measured using a UV light source with the red, green and blue filtered photodiodes. This is in contrast to Comparative Example 3, a CD not containing the fluorescent taggant, which showed very little fluorescence emission, particularly as measured with the green filtered photodiode. It is contemplated that the kiosk can use the information obtained from the detector to limit operation of the CD-R burner drive to only those CD-R discs that have a detector response that matches a predetermined value or range of values.

TABLE 2

| | Photodiode Intensity (a.u.) | | |
|---|---|---|---|
| | Red | Green | Blue |
| Sample Color Measurements | | | |
| White Reference (note: white label on label-side of CD) | 4070 | 4090 | 4067 |
| Comparative Example1 CD-R | 2675 | 2189 | 774 |
| Comparative Example2 CD | 2983 | 2064 | 744 |
| Comparative Example3 CD (note: no taggant) | 3041 | 2087 | 748 |
| Fluorescence Measurements | | | |
| Comparative Example1 CD-R | 577 | 1238 | 7612 |
| Comparative Example2 CD | 551 | 1079 | 7510 |
| Comparative Example3 CD (note: no taggant) | 256 | 162 | 6586 |

By using a method of authentication of user provided data storage media, a digital kiosk machine may either approve or deny use of the digital kiosk machine based upon the authenticatability of the user provided data storage media. The authenticatability of user provided data storage media may reduce the incidence of piracy and unauthorized reproduction of digital content that occurs in digital kiosk machines. The use of the detector in a digital kiosk machine with user provided data storage media may reduce the demand for certain digital kiosk machines to be regularly replenished with data storage media by a data storage media provider. The reduction and/or removal of a data storage media provider to digital kiosk machines may decrease the likelihood of provider theft and/or tampering with the digital kiosk machine because the digital kiosk machine would only allow recordation of digital content onto authenticatable data storage media, which could be obtained exclusive of the digital kiosk machine. This may reduce the incidence of piracy and unauthorized reproduction of both data storage media and digital content.

This authentication system can be used in various authentication applications. It can be used to authenticate data storage media wherein the authentication is determined from the read side and/or from the non-read side of the media. Additionally, depending upon the orientation and location of the energy sources (e.g., light sources) versus the sensing devices (e.g., light sensing devices), the system can operate in a reflection mode or a transmission mode. This system can also be designed and employed to authenticate other than data storage media, such as any medium having the desired fluorophore and color can be identified from a medium devoid of the desired fluorophore and color. Therefore the present system can be used to authenticate credit cards, debit cards, document (e.g., legal document such as a visa, social security card, birth certificate, driver's license, passport, or the like), identification (security) badge, and the like, wherein the authentic medium (e.g., authentic passport) has a film, layer, label, and/or substrate, individually, comprise the desired fluorophore and color.

This authentication system can also be used as a highly portable device for the authentication or sorting of polymers or polymeric articles comprising a color and luminescent tag. Note that depending on the nature and shape of the polymeric material or article to be authenticated, the system may need to be customized in order to optimize the size of the area to be tested and ensure the maximum sensitivity and detection capability.

Unlike systems that rely upon digital signals for authentication (e.g., a system that attempts to read data from a disc and subsequently re-attempts to read data from a disc, where a change in the color or fluorescence allows/inhibits the reading to occur and the ability to obtain certain digital data determines the authentication), the present system does not rely upon data being present on the disc. This system relies upon analog signals and a comparison of a known, desired analog signal with a received analog signal. Due to the combination of energy sources and sensing devices, a signal (e.g., a photoluminescent emission) can be received and used to authenticate the medium. Specifically, a combination of a photoluminescent emission and another analog response can be used to enable a more accurate authentication process. It is noted that the present authentication system can further employ a digital signal if desired. For example, a digital signal can be read from the medium or digital information can be disposed upon the medium, e.g., identifying when, where, how, etc., it was authenticated.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An authentication system, comprising:
    a first light source having a first light source spectral distribution and being capable of providing sufficient excitation to produce a photoluminescent emission from a medium comprising a luminescent tag and a color, wherein the photoluminescent emission has a photoluminescence intensity;
    a second light source having a visible multi-wavelength spectral distribution and being capable of providing sufficient visible multi-wavelength illumination of the medium to generate a second analog response, wherein the second analog response is different from the photoluminescent emission; and
    at least three optically filtered light sensing devices for detecting analog emission intensity in a spectral sensitivity range;
    wherein each light sensing device has a different device spectral sensitivity range which includes at least a portion of the visible multi-wavelength spectral distribution;
    wherein the device spectral sensitivity range of at least one of the light sensing devices includes at least a portion of a desired photoluminescent emission wavelength range; and
    wherein each light sensing device is configured to receive at least one of the photoluminescent emission and the second analog signal.

2. The authentication system of claim 1, further comprising a comparator in operable communication with the light sensing devices and capable of receiving a detected signature from the light sensing devices and of determining whether the detected signature is from an authentic medium.

3. The authentication system of claim 1, wherein at least one of the first light source and the second light source is a LED.

4. The authentication system of claim 3, wherein the first light source is a UV LED and the second light source is a visible LED.

5. The authentication system of claim 1, wherein the filtered light sensing devices are filtered photodiodes.

6. The authentication system of claim 5, wherein the device spectral sensitivity range of at least two of the filtered light sensing devices includes at least a portion of the desired photoluminescent emission wavelength range.

7. The authentication system of claim 6, wherein the device spectral sensitivity range of at least three of the filtered light sensing devices includes at least a portion of the desired photoluminescent emission wavelength range.

8. The authentication system of claim 5, wherein the first filtered photodiode is a green filtered photodiode, the second filtered photodiode is a blue filtered photodiode, and the third filtered photodiode is a red filtered photodiode.

9. The authentication system of claim 5, further comprising a fourth photodiode having a fourth spectral sensitivity range that is unfiltered in the visible multi-wavelength spectral distribution.

10. The authentication system of claim 5, further comprising
a fifth filtered photodiode having a fifth spectral sensitivity range that is different from the device spectral sensitivity ranges of the other filtered photodiodes;
wherein the first device spectral sensitivity range and the second device spectral sensitivity range are greater than or less than a desired peak emission wavelength;
the third device spectral sensitivity range includes the desired peak emission wavelength; and
wherein if the first spectral sensitivity range is greater than the desired peak emission wavelength then the fifth spectral sensitivity range is less than the desired peak emission wavelength, and if the first spectral sensitivity range is less than the desired peak emission wavelength then the fifth spectral sensitivity range is greater than the desired peak emission wavelength.

11. The authentication system of claim 10, wherein the second light source includes a desired absorbed wavelength range, and wherein the fifth peak is in the desired absorbed wavelength range.

12. The authentication system of claim 5, wherein
the first photodiode has a first peak in a first wavelength range where the photoluminescent emission is at 10% to 70% of a maximum photoluminescence intensity;
the second photodiode has a second peak in a second wavelength range where the photoluminescent emission is at 10% to 70% of the maximum photoluminescence intensity; and
the third photodiode has a third peak in a third wavelength range where the photoluminescent emission is at 70% to 100% of the maximum photoluminescence intensity.

13. The authentication system of claim 5, further comprising at least one of
an eleventh photodiode having an eleventh spectral sensitivity range and having an eleventh peak that corresponds to a shortest wavelength of the desired photoluminescent emission wavelength range ±5 nm; and
a twelfth photodiode having a twelfth spectral sensitivity range and having a twelfth peak that corresponds to a longest wavelength of the desired photoluminescent emission wavelength range ±5 nm.

14. The authentication system of claim 5, wherein a thirteenth photodiode having an thirteenth spectral sensitivity range and having a thirteenth peak that is within 100 nm of a longest wavelength at which the desired photoluminescent emission wavelength range has an intensity of less than 1% of a maximum desired photoluminescence intensity.

15. The authentication system of claim 5, comprising a fourteenth optically filtered photodiode having a fourteenth spectral sensitivity range that includes the first light source spectral distribution.

16. The authentication system of claim 1, wherein the light sensing devices, the first light source, and the second light source are disposed adjacent one another such that the photoluminescent emission and the second analog response can be received by the light sensing devices in a reflectance mode.

17. The authentication system of claim 1, further comprising a resistor in electrical communication with the light sensing devices.

18. The authentication system of claim 1, further comprising a calibration surface designed and located to enable the authentication system to internally calibrate.

19. The authentication system of claim 2, further comprising a temperature sensor in thermal communication with at least one of the light sensing devices and in operable communication with the comparator.

20. The authentication system of claim 4, wherein the visible LED is a white light LED.

21. The authentication system of claim 4, wherein the visible LED is a white LED having a CIE 1931 chromaticity x=0.25 to 0.33 and y=0.21 to 0.42.

22. The authentication system of claim 10, wherein the fifth spectral sensitivity range is equal to the fifth peak ±30 nm.

23. The authentication system of claim 22, wherein the fifth peak corresponds to a photoluminescence peak intensity of the photoluminescence emission ±20 nm.

24. The authentication system of claim 23, wherein the fifth peak corresponds to the photoluminescence peak intensity ±10 nm.

25. The authentication system of claim 24, wherein the fifth peak corresponds to the photoluminescence peak intensity ±5 nm.

26. The authentication system of claim 10, further comprising
a sixth photodiode having a sixth spectral sensitivity range equal to a sixth peak ±30 nm; and
a seventh photodiode having a seventh spectral sensitivity range equal to a seventh peak ±30 nm;
wherein the sixth spectral sensitivity range, the seventh spectral sensitivity, the fifth spectral sensitivity range, and the device spectral sensitivity ranges are different from each other.

27. The authentication system of claim 15, wherein the fourteenth photodiode is a UV photodiode.

28. The authentication system of claim 14, wherein thirteenth peak that is within 50 nm of a longest wavelength at which the photoluminescence emission band has an intensity of less than 1% a maximum photoluminescence intensity.

29. A data device, comprising:
an authentication analog measurement device capable of generating a detected analog signature of a data storage medium;
a comparator capable of determining if the detected analog signature is from an authentic medium, wherein the comparator is in operable communication with the measurement device; and
an information device capable of at least one of reading from and writing to the authentic medium, wherein the information device is in operable communication with the comparator;
wherein the measurement device further comprises
a first light source having a first light source spectral distribution and being capable of providing sufficient excitation to produce a photo luminescent emission from a medium comprising a luminescent tag and a color, wherein the photoluminescent emission has a photoluminescence intensity;
a second light source having a visible multi-wavelength spectral distribution and being capable of providing sufficient visible multi-wavelength illumination of the medium to generate a second analog response, wherein the second analog response is different from the photoluminescent emission; and at least three optically filtered light sensing devices for detecting analog emission intensity in a spectral sensitivity range;

wherein each light sensing device has a different device spectral sensitivity range which includes at least a portion of the visible multi-wavelength spectral distribution;

wherein the device spectral sensitivity range of at least one of the light sensing devices includes at least a portion of a desired photoluminescent emission wavelength range; and wherein each light sensing device confignred to receive at least one of the photoluminescent emission and the second analog signal.

30. The data device of claim 29, wherein the information device further comprises a laser and wherein at least one of the first light source and the second light source is the laser.

31. The data device of claim 29, wherein the measurement system is capable of detecting a desired color and a desired photoluminescence emission of the authentic medium.

32. A method of using a data device, comprising:

illuminating a tested medium with a first light source to produce a tested photoluminescent emission, wherein an authentic medium has an optical photoluminescence identifier with a desired photoluminescence intensity and a desired photoluminescence peak wavelength and has an optical color identifier, and wherein the tested photoluminescent emission has a tested photoluminescence intensity and a tested photoluminescence peak intensity;

illuminating the tested medium with a second light source in the visible wavelength range to produce a second analog response, wherein the second analog response is different from the tested photoluminescent emission;

determining a first intensity of the tested photoluminescent emission, wherein the first intensity is determined in a first wavelength range that includes the desired photoluminescence peak intensity;

determining a second intensity of the tested photoluminescent emission, wherein the second intensity is determined in a second wavelength range that is different than the first wavelength range;

determining a third intensity of the tested photoluminescent emission, wherein the third intensity is determined in a third wavelength range that is different than the first and second wavelength range;

determining if the first intensity, the second intensity, and the third intensity of the tested photoluminescent emission correspond to the optical photoluminescence identifier; and determining if the second analog response corresponds to the optical color identifier, wherein if the first intensity, the second intensity, and the third intensity correspond to the optical photoluminescence identifier and if the second analog response corresponds to the optical color identifier, the tested medium is authenticated as the authentic medium.

33. The method of claim 32, further comprising determining if a digital identifier is present on the data storage medium.

34. The method of claim 32, further comprising writing data to the authentic medium.

35. The method of claim 32, further comprising inhibiting the writing to a non-authentic medium.

36. The method of claim 32, further comprising inhibiting reading from a non-authentic medium.

37. The method of claim 32, wherein the photoluminescent emission is a fluorescence emission.

* * * * *